United States Patent
Kugimiya et al.

(10) Patent No.: US 7,858,036 B2
(45) Date of Patent: Dec. 28, 2010

(54) TASTE RECOGNITION APPARATUS AND TASTE RECOGNITION SYSTEM USING THE SAME

(75) Inventors: Yuichi Kugimiya, Maebaru (JP);
Yoshikazu Kobayashi, Atsugi (JP);
Ronggang Cheng, Atsugi (JP);
Hidekazu Ikezaki, Atsugi (JP);
Yoshinobu Naito, Odawara (JP)

(73) Assignee: Intelligent Sensor Technology, Inc., Atusugi-Shi (JP)

( * ) Notice: Subject to any disclaimer, the term of this patent is extended or adjusted under 35 U.S.C. 154(b) by 412 days.

(21) Appl. No.: 11/919,727

(22) PCT Filed: Dec. 27, 2006

(86) PCT No.: PCT/JP2006/326130

§ 371 (c)(1),
(2), (4) Date: Oct. 31, 2007

(87) PCT Pub. No.: WO2008/081524

PCT Pub. Date: Jul. 10, 2008

(65) Prior Publication Data

US 2010/0107785 A1    May 6, 2010

(51) Int. Cl.
*G01N 15/06* (2006.01)
*G01N 33/00* (2006.01)
*G01N 33/48* (2006.01)

(52) U.S. Cl. ............. 422/68.1; 422/82.01; 422/50; 422/82.02; 436/43; 436/63; 436/149; 204/193; 204/400

(58) Field of Classification Search ............. 422/68.1, 422/82.01
See application file for complete search history.

(56) References Cited

U.S. PATENT DOCUMENTS 5,302,262 A    4/1994    Yamaguji et al.
(Continued)

FOREIGN PATENT DOCUMENTS

EP    0 410 356 A1    1/1991
(Continued)

OTHER PUBLICATIONS

English language International Search Report dated Apr. 17, 2007, issued in a counterpart International Application.
(Continued)

*Primary Examiner*—Brian J Sines
(74) *Attorney, Agent, or Firm*—Holtz, Holtz, Goodman & Chick, PC

(57) ABSTRACT

A taste recognizing device has a sensor body and a touch panel. The sensor body includes a sensor part with a sensor probe for measuring taste by means of a molecular film which outputs an electrical signal presenting taste information representing at least one kind of taste, a solution insertion part having insertion sections which are arranged circumferentially at predetermined intervals and in which a solution whose taste is to be measured, a reference taste measurement solution and a cleaning solution are selectively inserted, and an arm drive part for moving the sensor part relative to a predetermined insertion section of the solution insertion part. On the basis of the electric signal outputted from the sensor probe and presenting the taste information, at least measurement for taste recognition of the solution whose taste is to be measured is made possible. The touch panel is structured so that all the items of the operations of the sensor body necessary for measurement for the taste recognition are indicated by buttons for each function and displayed in order on the screen, the operation item corresponding to the operation item is inputted when the user clicks a predetermined button, and thereby all the operations of the sensor body by the user are performed with reference to the display on the screen. With this, the taste recognizing device enables easy taste measurement of the substance whose taste is to be measured by easier operation as a whole.

24 Claims, 26 Drawing Sheets

U.S. PATENT DOCUMENTS

| | | | |
|---|---|---|---|
| 5,482,855 A | 1/1996 | Yamaguji et al. | |
| 5,789,250 A | 8/1998 | Ikezaki | |
| 6,290,838 B1 * | 9/2001 | Mifsud et al. | 205/775 |
| 6,391,645 B1 | 5/2002 | Huang et al. | |
| 7,550,080 B2 | 6/2009 | Morikawa | |

FOREIGN PATENT DOCUMENTS

| | | |
|---|---|---|
| EP | 0 464 820 A1 | 1/1992 |
| EP | 0 763 729 A1 | 3/1997 |
| JP | 4-57421 A | 2/1992 |
| JP | 2578370 B2 | 11/1996 |
| JP | 10-318963 A | 12/1998 |
| JP | 11-101773 A | 4/1999 |
| JP | 3037971 B2 | 2/2000 |
| JP | 2000-146896 A | 5/2000 |
| JP | 2001-14583 A | 1/2001 |
| JP | 3313433 B2 | 5/2002 |
| JP | 2002-214185 A | 7/2002 |
| JP | 2003-5821 A | 1/2003 |
| JP | 2003-190956 A | 7/2003 |
| JP | 2005-43121 A | 2/2005 |
| JP | 2006-172148 A | 6/2006 |
| JP | 2006-515929 A | 6/2006 |
| JP | 2006-234459 A | 9/2006 |
| JP | 2006-258732 A | 9/2006 |
| JP | 2006-266939 A | 10/2006 |
| JP | 2006-284380 A | 10/2006 |
| WO | WO 96/30753 A1 | 10/1996 |
| WO | WO 03/100057 A1 | 12/2003 |

OTHER PUBLICATIONS

International Preliminary Report on Patentability and Written Opinion of the International Searching Authority dated Jul. 9, 2009 (6 pages), issued in counterpart International application No. PCT/JP2006/326130.

Japanese Office Action dated Aug. 24, 2010 and English translation thereof in counterpart Japanese Application No. 2007-541543.

* cited by examiner

FIG. 10

Taste recognition apparatus management system

Select place of storage

Select place to store measurement conditions.
If already registered, overwritten.

| Select | Pattern name | Measurement procedure name | Sensor setting name | Sample setting name | Place of storage |
|---|---|---|---|---|---|
| ○ | Maintenance measurement | | | | 0 |
| ○ | Measurement pattern 1 | | | | 1 |
| ○ | Measurement pattern2 | | | | 2 |
| ○ | Measurement pattern3 | | | | 3 |
| ○ | Measurement pattern4 | | | | 4 |
| ○ | Measurement pattern5 | | | | 5 |
| ○ | Temporary measurement | | | | WORK |

[Return]   [To next step]

FIG. 12

TASTE RECOGNITION APPARATUS AND TASTE RECOGNITION SYSTEM USING THE SAME

This application is a U.S. National Phase Application under 35 USC 371 of International Application PCT/JP2006/326130 filed Dec. 27, 2006.

TECHNICAL FIELD

The present invention relates to a taste recognition apparatus and a taste recognition system using the apparatus, and particularly to a taste recognition apparatus and a taste recognition system using the apparatus employing a technique to facilitate both the taste measurement of a sample substance with a simpler overall operation and the analytical evaluation of the taste measurement result while keeping a high maintainability using a taste sensor device with lipid molecular films and a taste sensing system using the sensor device.

BACKGROUND ART

In recent years, a taste sensor device with lipid molecular films and a taste sensing system using the device have been developed as a taste recognition apparatus and a taste recognition system using the apparatus. The device and the system are capable of detecting, evaluating by quantifying the taste of food or the like and visually displaying the detection result on a graph or the like using a taste sensor with lipid molecular films of an amphiphatic substance or a bitter substance, for example, as a replacement of gustation, one of the five senses of the human being.

Patent Document 1, Patent Document 2, Patent Document 3 and Patent Document 4 described later are known, for example, as patents granted to Anritsu Co., Ltd. et al. who have transferred the business thereof to the present applicant or the assignee thereof with regard to the aforementioned taste sensing system with lipid molecular films.

All the patent rights on the taste sensing system with lipid molecular films including those of Patent Documents 1 to 4 are assigned to the present applicant or the assignee of this application from Anritsu Co., Ltd.

In order to facilitate the understanding of this invention, the gist of the contents of Patent Documents 1 to 4 will be briefly explained below.

First, Patent Document 1 filed earliest of all the cited patent documents indicates that lipid molecular films constitute a taste sensor adapted to work as a replacement of human taste. Each of lipid molecular films has a structure in which a lipid substance (of which the amphiphatic substance is a kind) with molecules having both a hydrophobic portion and a hydrophilic portion is fixed in a high-polymer matrix and the hydrophilic portion is aligned on the surface thereof. Patent Document 1 also discloses a specific taste sensing system using the taste sensor.

FIG. 20 is a diagram, shown by an expression method used to design chemical substances, for explaining a model of the lipid molecular films disclosed in Patent Document 1 as a conventional taste recognition apparatus.

In FIG. 20, spherical portions of the lipid molecules indicated by circles each designate a hydrophilic group a, i.e. a hydrophilic portion a from which a long chain structure b (such as an alkyl group) of hydrocarbon extends as an atomic arrangement.

In all cases shown in FIG. 20, two chains extend as one molecule and a molecule group is formed by the molecules as a whole. The portion of hydrocarbon in chain form constitutes a hydrophobic portion b.

This lipid molecule group 31 is accommodated in a matrix 33 (surface structure or a micro structure having a planar expansion), though partly penetrated into the matrix (for example, designated by reference numeral 31' in FIG. 20), on the surface of a film member 32. The lipid molecule group 31 is thus accommodated with the hydrophilic portion arranged on the surface.

FIG. 21A is a sectional view shown for explaining three sensory units of an array electrode of a multi-channel taste sensor formed of the lipid molecular films disclosed in Patent Document 1 as a conventional taste recognition apparatus.

FIG. 21B is a plan view shown for explaining three sensory units of an array electrode of a multi-channel taste sensor formed of the lipid molecular films disclosed in Patent Document 1 as a conventional taste recognition apparatus.

In the case shown in FIGS. 21A, 21B, holes of 0.5 mmϕ are formed through an acrylic base member 1, in which round silver rods are inserted as electrodes 2 each connected with a lead wire 5 by solder 6, while a lipid molecular film 3 is attached on the base member 1 in contact with the electrodes 2 through a buffer layer 4.

FIG. 22 is a block diagram shown for explaining a taste measurement system using the aforementioned multi-channel taste sensor disclosed in Patent Document 1 as a conventional taste recognition apparatus.

First, an aqueous solution of a sample substance is prepared and, as a sample solution 11, placed in a container 12 such as a beaker.

A taste sensor array 13 produced by arranging a lipid film and an electrode on the acrylic plate (base member) as described above is placed in the sample solution 11.

Before use, the electrode potential is stabilized with an aqueous solution of potassium chloride 1 mmol/l.

In FIG. 22, reference numerals 14-1, ..., 14-8 designate the lipid films 3 as black points.

A reference electrode 15 is prepared for generating a reference potential for measurement, and placed in the sample solution 11.

The taste sensor array 13 and the reference electrode 15 are arranged in predetermined spaced relation with each other.

The surface of the reference electrode 15 is covered with a buffer layer 16 formed of potassium chloride 100 mmol/l solidified by agar. Therefore, the electrode system is configured of silver 2| silver chloride 4| lipid film 3 (14)| sample solution 12| buffer layer (potassium chloride 100 mmol/l) 16| silver chloride 4| silver 2.

The electrical signal from each lipid film 3 makes up 8-channel signals in FIG. 22, which are led by lead wires 17-1, ..., 17-8 to buffer amplifiers 19-1, ..., 19-8, respectively.

The outputs of the buffer amplifiers 19-1, ..., 19-8 are selected by an analog switch (8 channels) 20 and applied to an analog/digital (A/D) converter 21.

The electrical signal from the reference electrode 15 is also applied to the A/D converter 21 through the lead wire 18, and the difference with the potential of the film is converted into a digital signal.

This digital signal is properly processed for the arithmetic operation required for taste measurement in a microcomputer 22 and displayed on an X-Y recorder 23.

In the case shown in FIG. 22, an 8-channel taste sensor is used, and the films used for each channel contains 11 types of lipid molecular film, as shown below, having different taste response characteristics to obtain taste information sufficiently great in amount to reproduce the human taste.

| No. | Lipid substance |
| --- | --- |
| 1 | Dioctyl phosphate |
| 2 | Cholesterol |
| 3 | Trioctylmethyl ammonium chloride |
| 4 | Oleic acid |
| 5 | n-octadecyl chloride |
| 6 | Diphenyl phosphate |
| 7 | Decyl alcohol |
| 8 | Dioctadecyl dimethyl ammonium bromide |
| 9 | Lethicin |
| 10 | Trimethyl stearyl ammonium chloride |
| 11 | Oleyl amine |

The taste sensor described in Patent Document 1, which is a taste sensor in the true sense of the words, has the physicochemical quality similar to the tongue, i.e. the gustatory organ of the human being, and can produce a similar output for a similar taste in spite of a different sample substance while at the same time producing some output for a different taste.

Next, Patent Document 2 discloses a method of detecting the taste using the taste sensor described in Patent Document 1.

The invention relating to the taste detection method disclosed in Patent Document 2 makes it possible to identify even the delicate difference in taste such as the brand difference and the lot difference of beer and other foods. This taste detection method will be described briefly below.

Specifically, according to this taste detection method, a reference liquid similar to a sample liquid is used to secure a high reproducibility for detection and measurement of the taste by the taste sensor using lipid molecular films.

The taste sensor is dipped sufficiently in this reference liquid, and a similar stimulus is applied for each measurement using the taste sensor.

The time of measurement is selected at an appropriate time when the internal potential slowly changes after stabilization of the surface potential, and the difference in the measurement value between the reference liquid and the sample liquid is calculated.

In the case where the sample is beer, the beer or a substance similar to the beer is used as a reference liquid. The taste sensor is dipped in this reference liquid in advance and familiarized with the reference liquid.

As a result, an adsorptive substance is adsorbed in advance to the lipid film contained in the beer, and therefore, the effect of the adsorptive substance on the measurement of various types of beer is reduced.

This taste detection method has the advantage that the reproducibility is highly improved although the sensitivity to a substance having the adsorptive property to the lipid film is reduced.

Next, Patent Document 3 discloses a taste detection method advanced from the method for detecting the taste using the taste sensor described in Patent Document 2.

In the taste detection method according to a first aspect of the invention disclosed in Patent Document 3, in order to carry out the taste detection and measurement with a high reproducibility by the taste sensor using the molecular film of the amphiphatic or bitter substance containing the lipid film described above (hereinafter briefly referred to as the molecular film), a first reference liquid and a second reference liquid similar to the sample liquid are used. Then, by calculating the value $((V_s-V_0')-(V_k-V_0))$ relative to the reference value of the sample liquid measurement taken for the first reference liquid ($V_0$), the second reference liquid ($V_k$), the first reference liquid ($V_0'$) and the sample liquid ($V_s$) in that order, the variation in the relative value in the sustained drift of the taste sensor is eliminated. At the same time, by using the first reference liquid, the effect on the measurement value can be eliminated even in the case where the taste of the first reference liquid undergoes a change.

In the case where the taste of the sample solution containing an adsorptive substance is measured using the taste sensor having the molecular film of an amphiphatic or bitter substance as described above, a first measurement value obtained by the taste sensor with no adsorptive substance adsorbed to lipid molecular films is different from a second measurement value obtained by the taste sensor with the adsorptive substance adsorbed to lipid molecular films. Although the difference is gradually decreased, the measurement value is different between the second and third measurement sessions, between the third and fourth sessions, and so forth.

In such a case, the adsorptive substance should better be removed from the molecular film. For lack of the proper method of removal, however, the measurement of the sample solution containing the substance adsorptive to the molecular film is conducted by the taste sensor using the molecular film in such a manner that before measurement of the sample solution, a reference liquid having components similar to the sample solution is prepared, and by sufficiently dipping the taste sensor in the reference liquid, the substance adsorptive to the molecular film in the reference liquid is adsorbed in advance.

By doing so, this taste detection method reduces (stabilizes) the effect of the adsorptive substance at the time of measurement and thereby improves the reproducibility.

According to the taste detection method described in Patent Document 3, in order to improve (stabilize) the reproducibility, the taste sensor is sufficiently dipped in a liquid having a similar component to the sample solution as a pre-measurement stage, and the substances adsorptive to the film (lipid molecular film) are adsorbed in advance of measurement. (1) This poses the problem, therefore, that the sensitivity to a sample substance such as bitterness high in adsorption is reduced.

Regardless of adsorption of an adsorptive substance before measurement, a different type of lipid molecular films used for the taste sensor has a different amount of response to a basic taste such as sourness, saltiness, sweetness, bitterness or flavor.

Also, the lipid molecular films respond to a plurality of basic tastes. For example, a certain lipid molecular film responds not only to sourness but also to bitterness to one degree to another. Therefore, the ratio of response to each basic taste to the total response amount of a particular molecular film is unknown.

In addition, the advanced adsorption to an adsorptive substance makes the film surface of all the taste sensors become analogous to each other, and so the response to each basic taste becomes similar.

Thus, (2) the problem is posed that it becomes more difficult to decompose the response to each basic taste.

The aforementioned problems of the taste measurement method described in Patent Document 3 lead to the availability of a smaller amount of information on taste.

Next, Patent Document 4 discloses a taste measurement method for measuring the taste using a taste sensor with lipid molecular films which obviates the problems of the taste detection method for detecting the taste using the taste sensor described in Patent Document 3.

In the taste measurement method described in Patent Document 4, the desired reference liquid is prepared, a sensor potential V01 with a first reference liquid is measured, and the sensor is dipped for a predetermined time in a sample solution containing an ionizable adsorptive substance, after which a sensor potential V02 in a second reference liquid is measured and the difference is determined between V01 and V02.

Also, in this taste measurement method, the second reference liquid is used which is lower in at least one of sourness and saltiness, i.e., at least 0.3 higher in pH hydrogen ion index (pH) and/or one half or lower in electric conductivity than the first reference liquid.

Also, in this taste measurement method, the taste sensor is cleaned before measuring the sensor potential V02 with the second reference liquid, for example.

With any desired reference liquid described above containing no ionizable adsorptive substance, any sample solution is measurable.

This is because, in such a reference liquid, no ionizable adsorptive substance is adsorbed to the molecular film when the taste sensor is dipped in it.

An aqueous solution containing only acid and/or salt and such an aqueous solution with a sweet flavor added thereto are some examples.

A reference liquid containing the same ionizable adsorptive substance as the sample solution in such a small amount as not to affect the taste measurement of the sample solution can be employed.

Even in the case where the ionizable adsorptive substance is adsorbed to the molecular film with the taste sensor dipped in the reference liquid, no problem is posed as long as the amount so adsorbed is ignorable as compared with the amount adsorbed when dipped for a predetermined time in the sample solution.

In the taste measurement method described above, the sensor potential of the first reference liquid is set to V01 and the sensor potential of the second reference liquid after dipping in the sample solution (sample liquid) to V02.

In the absence of an ionizable substance adsorptive to the molecular film in the sample liquid, V02 is substantially equal to V01.

To simplify the description below, the first and second reference liquids are assumed to contain the same components.

In the presence of an ionizable substance adsorptive to the molecular film, on the other hand, the ionizable adsorptive substance adsorbed to the surface of the molecular film works as a fixed charge of the molecular film. The film potential changes with the density of the fixed charge.

Even in the case where the same reference liquid is measured, the film potential is varied between the cases in which an ionizable adsorptive substance is adsorbed and not adsorbed to the surface of the molecular film, and therefore, V01 and V02 are different from each other.

The difference between V01 and V02 corresponds to the amount of adsorption of the ionizable adsorptive substance to the film.

The time for dipping in the sample solution being constant, the amount of adsorption of an ionizable adsorptive substance to the film corresponds to the density of the ionizable adsorptive substance contained in the sample solution. By measuring V01, V02 and determining the difference therebetween, therefore, the information on the taste presented by the ionizable adsorptive substance of the sample solution is obtained.

Also, by employing a liquid weaker in taste than the first reference liquid as a second reference liquid, the measurement sensitivity is improved.

In other words, even in the case where the measurement of two sample liquids shows the same difference of the amount adsorbed to the film, the difference in measurement value is larger in the case where the second reference liquid is weaker in taste than the first reference liquid.

In the case where the taste sensor is cleaned before measuring the sensor potential V02 with the second reference liquid, only a substance adsorbed with not less than a certain level of strength is left and the taste information on the remainder can be obtained by selecting the degree of strength of cleaning, the type of cleanser, etc.

Next, a taste recognition system to which the taste measurement method described in Patent Document 4 is applied will be briefly explained.

A batch-type taste recognition system as shown in FIGS. 23 to 27A, 27B includes a detector/handler unit 101 and a data processing unit 102.

FIG. 23 is a perspective view shown for explaining the configuration of the batch-type taste recognition system disclosed in Patent Document 4 as a conventional taste recognition apparatus.

As shown in FIG. 23, the detector/handler unit 101 includes a measurement table 101a, a robot proper 101b, a robot drive unit 101c and a container mounting plate 101d.

A sensor unit 101e is mounted at the forward end of the robot proper 101b.

FIG. 24 is a perspective view shown for explaining the configuration of the sensor unit 101e of the batch-type taste recognition system disclosed in Patent Document 4 as a conventional taste recognition apparatus.

The sensor unit 101e, as shown in FIG. 24, includes a buffer amplifier 101f, a sensor support unit 101g, a sensor guard 101h, a photosensor 101i, a plurality of sensor probes 101j and a reference electrode 101k.

FIG. 25A is a side view shown for explaining the configuration of the sensor probes 101j of the sensor unit 101e in the batch-type taste recognition system disclosed in Patent Document 4 as a conventional taste recognition apparatus.

FIG. 25B is a side view shown for explaining the configuration of the reference electrode 101k of the sensor unit 101e in the batch-type taste recognition system disclosed in Patent Document 4 as a conventional taste recognition apparatus.

The sensor probes 101j and the reference electrode 101k, as shown in FIGS. 25A, B, each include a probe proper 1011, an electrode terminal 101m, an Ag/AgCl electrode 101n and an internal liquid (saturated AgCl, 3.3 MKCl) 101o.

A lipid substance film 101p is arranged at the forward end of each sensor probe 101j.

A saturated KCl agar 101q is arranged at the forward end of the reference electrode 101k.

The data processing unit 102 includes a rack proper 102a, a power supply box 102b, a personal computer 102c, an operation unit 102d and a display unit 102e.

FIG. 26 is a block diagram shown for explaining the configuration of the control system of the batch-type taste recognition system disclosed in Patent Document 4 as a conventional taste recognition apparatus.

FIG. 27A is a perspective view shown for explaining automatic measurement conducted by dipping the sensor unit 101e in a reference liquid container, a passivation liquid container, a cleanser container and a measurement liquid (sample liquid) container mounted in a predetermined form on the container mounting plate 101d of the batch-type taste recognition system disclosed in Patent Document 4 as a conventional taste recognition apparatus.

Incidentally, FIG. 27A shows the automatic measurement conducted by using a sample cleanser with the passivation liquid and the reference liquid being different from each other.

FIG. 27B is a perspective view shown for explaining the automatic measurement conducted by dipping the sensor unit 101e in the reference liquid container, the passivation liquid container, the cleanser container and the measurement liquid (sample liquid) container mounted in a predetermined form on the container mounting plate 101d of the batch-type taste recognition system disclosed in Patent Document 4 as a conventional taste recognition apparatus.

Incidentally, FIG. 27B shows the automatic measurement conducted without using the sample cleanser with the passivation liquid and the reference liquid being identical with each other.

In the batch-type taste recognition system having this configuration, as shown in FIG. 26, the automatic measurement is conducted with the robot proper 101b of the detector/handler unit 101 controlled by the personal computer 102c while the sensor unit 101e is dipped in the reference liquid container, the passivation liquid container, the cleanser container, the measurement liquid (sample liquid) container and the like mounted in a predetermined form on the container mounting plate 101d, as shown in FIGS. 27A, B.

The data processing unit 102, with the data from the sensor unit 101e subjected to A/D conversion and fetched into the personal computer 102c for analysis of the main component, finally recognizes the taste of the sample liquid and outputs the taste information.

Under the circumstances, however, even the taste sensing system with lipid molecular films as the conventional taste recognition apparatus and the taste recognition system using the apparatus developed through the process as disclosed in Patent Documents 1 to 4 described above still encounter many problems to be solved as described below.

Desirably, for example, in the taste sensing system with lipid molecular films as viewed from the operator as a user, the taste of a sample substance can be measured with a simple operation while at the same time making it possible to easily analyze and evaluate the taste measurement result following a procedure in which it is easy to understand what is going on.

Also, the taste sensing system with lipid molecular films as viewed from the operator as a user has preferably such a high maintainability that the point of a trouble, if any occurs, can be grasped and solved easily.

Further, from the viewpoint of the user as a quality controller of the sample taste substance, the taste sensing system with lipid molecular films desirably has the operating ease with which the taste measurement can be readily conducted individually by a normal operator at a plurality of points on the production line. At the same time, a simple network is desired for collective centralized management of the analysis and evaluation data on the individual taste measurement results at a management center terminal.

In spite of a version-up, if any, of the OS of the personal computer used as a terminal, the correction of the software of the taste sensing system with lipid molecular films is desirably not required.

Also, it is desired from the viewpoint of the user as a quality controller of the sample taste substance that the efficient maintenance for the taste sensing system with lipid molecular films can be conducted using a network.

Also, what is desired by a researcher as a user of the taste sensing system with lipid molecular films is a superior function with a sophisticated analytical ability satisfactory for research purposes, while the operation thereof is easy even for laboratory assistants.

In this case, the taste sensing system with lipid molecular films as viewed from a commodity planning division as a user desirably has the appropriate ability to express the matters related to quality control as a commodity of which the analysis result can be used for marketing.

Specifically, in the taste sensor apparatus with lipid molecular films and the taste sensing system using the apparatus, which make up the aforementioned taste recognition apparatus and the taste recognition system using the apparatus as a whole, it is desirable that the taste of the sample taste substance can be measured with a simpler operation and the result of the taste measurement can be easily analyzed and evaluated while at the same time securing a high maintainability.

Patent Document 1: U.S. Pat. No. 5,482,855 (corresponding to JP 2,578,370, EP 410,356)
Patent Document 2: U.S. Pat. No. 5,302,262 (corresponding to JP 3,037,971, EP 464,820)
Patent Document 3: JP 3,313,433
Patent Document 4: U.S. Pat. No. 5,789,250 (corresponding to JP 3,547,760, EP 763,729)

DISCLOSURE OF INVENTION

An object of the present invention is to provide, in keeping with the demand to solve the problems of the background art described above, a taste recognition apparatus and a taste recognition system using the apparatus implemented by a taste sensor device with lipid molecular films and a taste sensing system using the device having a high maintainability and employing a technique for facilitating both the taste measurement of a sample taste substance with a simpler operation as a whole and the analysis and evaluation of the result of the taste measurement.

In view of this, the concept for development of the taste recognition apparatus and the taste recognition system using the apparatus according to this invention includes the following:

a) The measurement and evaluation for taste recognition can be carried out with a simple operation.

With regard to this point, a touch panel with a graphic user interface (GUI) of wizard type, for example, is employed to permit intuitive user operation and prevent the operating error reliably while at the same time simplifying the otherwise complicated analysis by automatic analysis of the measurement result.

b) The centralized management can be easily introduced to meet the network requirements.

With regard to this point, the taste recognition apparatus and the taste recognition system using the apparatus are connected by a network such as LAN to eliminate the need of an excessive environmental facility maintenance and make it possible to manage a plurality of taste recognition apparatuses with a single management server. Also, the application is made easily installable in a Servlet form for the measurement setting and the measurement result analysis in each taste recognition apparatus.

c) The measurement result is analyzed with a sophisticated analysis function to obtain a better result.

With regard to this point, the function of analyzing the measurement result for taste recognition is strengthened on the one hand and the graph function to output the analysis result is improved.

d) A high stability is exhibited to secure the constant operability of the taste recognition apparatus and the taste recognition system using the apparatus.

With regard to this point, for example, a Linux processor (server) having a high stability as a working CPU is employed in two systems, and the constant operability of the system as a whole is secured by processing the functions distributively.

Specifically, according to a first aspect of the present invention, in order to achieve the above-described object, there is provided a taste recognition apparatus comprising:

a sensor proper (212) including a sensor unit (215) provided with sensor probes (101j) for taste measurement with lipid molecular films which output electrical signals presenting taste information much than at least one type, a solution insertion unit (213) provided with a plurality of inserting portions (321) arranged at predetermined intervals along a circumference for selective insertion of a sample taste solution, a standard sample solution and a cleaning solution, and an arm drive unit (214) which moves the sensor unit (215) to a predetermined inserting portion (321) of the solution insertion unit (213), wherein based on the electrical signals presenting the taste information output from the sensor probes (101j), measurement for taste recognition of at least the sample taste solution is made possible; and a touch panel (211) so configured that all operation items required for the measurement for taste recognition on the sensor proper (212) are indicated by buttons with respective functions and sequentially displayed on a screen, and when a user designates a predetermined button, a corresponding one of the operation items can be input, thereby permitting the user to perform all the operations on the sensor proper (212) based on displaying on the screen.

According to a second aspect of the present invention, in order to achieve the above-described object, there is provided the taste recognition apparatus according to the first aspect, wherein the sensor unit (215) is supported movably along the direction of arrangement of the solution insertion unit (213) by the arm drive unit (214) vertically of the plurality of inserting portions (321) at a lower part of a forward end of an arm-like sensor board (233) arranged on a part of the arm drive unit (214) extending horizontally from an upper portion thereof, and potential differences generated by dipping the sensor probes (101j) of the sensor unit (215) into the sample taste solution and the standard sample solution inserted in a predetermined one of the plurality of inserting portions (321) are converted by an electrical circuit portion of the arm-like sensor board (233) into digital data as the electrical signals presenting the taste information and adapted to be sent out in a serial form to a CPU board (234) which controls the sensor proper (212) as a whole.

According to a third aspect of the present invention, in order to achieve the above-described object, there is provided the taste recognition apparatus according to the second aspect, wherein a processor (341) mounted on the CPU board (234) is of autonomous control type.

According to a fourth aspect of the present invention, in order to achieve the above-described object, there is provided the taste recognition apparatus according to the first aspect, wherein displaying on the touch panel (211) is a graphic user interface (GUI) of wizard type.

According to a fifth aspect of the present invention, in order to achieve the above-described object, there is provided the taste recognition apparatus according to the second aspect, wherein the processor (341) mounted on the CPU board (234) is adapted to carry out at least one of gain and offset calibration of an amplifier (331) arranged in the electrical circuit portion of the arm-like sensor board (233), calibration of a temperature sensor (240) arranged in the sensor unit (215) and position adjustment by a position sensor (239) arranged in the sensor unit (215).

According to a sixth aspect of the present invention, in order to achieve the above-described object, there is provided the taste recognition apparatus according to the second aspect, wherein the processor (341) mounted on the CPU board (234) has a self-diagnosis function of performing at least one of hardware check including periodic confirmation of a trouble of the electrical circuit portion of the arm-like sensor board (233) and connection/disconnection of a wire of each part and monitoring of a trouble of the measurement result of the sensor unit (215).

According to a seventh aspect of the present invention, in order to achieve the above-described object, there is provided the taste recognition apparatus according to the sixth aspect, wherein the processor (341) mounted on the CPU board (234), due to the self-diagnosis function thereof, is adapted to issue an alarm upon detection of a trouble of each part and thus prompts a user to conduct a required maintenance work.

According to an eighth aspect of the present invention, in order to achieve the above-described object, there is provided the taste recognition apparatus according to the fourth aspect, wherein the screen displayed on the touch panel (211) has a screen for designating arrangement of samples including the sample taste solution and the standard sample solution and arrangement of the cleaning solution in the plurality of inserting portions (321) of the solution insertion unit (213).

According to a ninth aspect of the present invention, in order to achieve the above-described object, there is provided the taste recognition apparatus according to the first aspect, wherein the taste measurement conducted by the sensor unit (215) includes a normal measurement mode, a maintenance measurement mode carried out before the normal measurement mode and a sensor check mode carried out before the maintenance measurement mode, the sensor check mode is carried out to confirm whether the taste measurement can be properly conducted by the sensor unit (215) or not, mode control is passed to the normal measurement mode upon confirmation that the taste measurement can be properly carried out by the sensor unit (215) in the execution of the sensor check mode, the mode control is passed to the maintenance measurement mode upon confirmation of "NG", i.e. that the taste measurement cannot be properly carried out by the sensor unit (215) in the execution of the sensor check mode, and the maintenance measurement mode is such that basic measurement and basic measurement analysis for analyzing a result of the basic measurement are carried out on the standard sample solution, and based on a result of the basic measurement analysis, the sensor probe (101j) of the sensor unit (215) is cleaned thereby to carry out the sensor check mode again.

According to a tenth aspect of the present invention, in order to achieve the above-described object, there is provided the taste recognition apparatus according to the first aspect, wherein the touch panel (211) is arranged independently of the sensor proper (212).

According to an eleventh aspect of the present invention, in order to achieve the above-described object, there is provided a taste recognition system comprising:

a sensor proper (212) including a sensor unit (215) provided with sensor probes (101j) for taste measurement with lipid molecular films which output electrical signals presenting taste information much than at least one type, a solution insertion unit (213) provided with a plurality of inserting portions (321) arranged at predetermined intervals along a circumference for selective insertion of a sample taste solution, a standard sample solution and a cleaning solution, and an arm drive unit (214) which moves the sensor unit (215) to a predetermined inserting portion (321) of the solution insertion unit (213), wherein based on the electrical signals presenting the taste information output from the sensor probes (101j), measurement for taste recognition of at least the sample taste solution is made possible;

a touch panel (211) so configured that all operation items required for the measurement for taste recognition on the sensor proper (212) are indicated by buttons with respective functions and sequentially displayed on a screen, and when a user designates a predetermined button, a corresponding one of the operation items can be input, thereby permitting the user to perform all the operations on the sensor proper (212) based on displaying on the screen; and a server (220) provided with a data base (223) which is installed with a measurement setting application (224) required for the measurement for taste recognition of the sensor proper (212) and an analysis application (225) required to analyze a result of the measurement for taste recognition by the sensor proper (212), and has stored therein various data required for the measurement for taste recognition and various data required to analyze the result of the measurement for taste recognition.

According to a twelfth aspect of the present invention, in order to achieve the above-described object, there is provided the taste recognition system according to the eleventh aspect, further comprising at least one management terminal (227) which carries out various settings for the taste recognition by the sensor proper (212) by accessing the server (220) through a network (226) and retrieving the measurement setting application (224) and the analysis application (225) installed in the server (220), while at the same time making it possible to carry out analysis of the result of the measurement for taste recognition by the sensor proper (212).

According to a thirteenth aspect of the present invention, in order to achieve the above-described object, there is provided the taste recognition system according to the eleventh aspect, wherein in the case where the sensor proper (212) and the touch panel (211) make up a taste sensor device (210) with lipid molecular films as one taste recognition apparatus, one server (220) is connected with a plurality of taste sensor devices (210, 210, . . . ) with lipid molecular films as a plurality of taste recognition apparatuses, and the taste sensor devices (210, 210, . . . ) with lipid molecular films as the plurality of taste recognition apparatuses are centrally managed by a single of the server (220).

According to a fourteenth aspect of the present invention, in order to achieve the above-described object, there is provided the taste recognition system according to the eleventh aspect, wherein the sensor unit (215) is supported movably along the direction of arrangement of the solution insertion unit (213) by the arm drive unit (214) vertically of the plurality of inserting portions (321) at a lower part of a forward end of an arm-like sensor board (233) arranged on a part of the arm drive unit (214) extending horizontally from an upper portion thereof, and potential differences generated by dipping the sensor probes (101j) of the sensor unit (215) into the sample taste solution and the standard sample solution inserted in a predetermined one of the plurality of inserting portions (321) are converted by an electrical circuit portion of the arm-like sensor board (233) into digital data as the electrical signals presenting the taste information and adapted to be sent out in a serial form to a CPU board (234) which controls the sensor proper (212) as a whole.

According to a fifteenth aspect of the present invention, in order to achieve the above-described object, there is provided the taste recognition system according to the fourteenth aspect, wherein a processor (341) mounted on the CPU board (234) is of autonomous control type.

According to a sixteenth aspect of the present invention, in order to achieve the above-described object, there is provided the taste recognition system according to the eleventh aspect, wherein displaying on the touch panel (211) is a graphic user interface (GUI) of wizard format.

According to a seventeenth aspect of the present invention, in order to achieve the above-described object, there is provided the taste recognition system according to the fourteenth aspect, wherein the processor (341) mounted on the CPU board (234) is adapted to carry out at least one of gain and offset calibration of an amplifier (331) arranged in the electrical circuit portion of the arm-like sensor board (233), calibration of a temperature sensor (240) arranged in the sensor unit (215) and position adjustment by a position sensor (239) arranged in the sensor unit (215).

According to an eighteenth aspect of the present invention, in order to achieve the above-described object, there is provided the taste recognition system according to the fourteenth aspect, wherein the processor (341) mounted on the CPU board (234) has a self-diagnosis function of performing at least one of hardware check including periodic confirmation of a trouble of the electrical circuit portion of the arm-like sensor board (233) and connection/disconnection of a wire of each part on the one hand and monitoring of a trouble of the measurement result of the sensor unit (215) on the other hand.

According to a nineteenth aspect of the present invention, in order to achieve the above-described object, there is provided the taste recognition system according to the eighteenth aspect, wherein the processor (341) mounted on the CPU board (234), due to the self-diagnosis function thereof, is adapted to issue an alarm upon detection of a trouble of each part and thus prompts a user to conduct a required maintenance work.

According to a twentieth aspect of the present invention, in order to achieve the above-described object, there is provided the taste recognition system according to the sixteenth aspect, wherein the screen displayed on the touch panel (211) has a screen for designating arrangement of samples including the sample taste solution and the standard sample solution and arrangement of the cleaning solution in the plurality of inserting portions (321) of the solution insertion unit (213).

According to a twenty-first aspect of the present invention, in order to achieve the above-described object, there is provided the taste recognition system according to the eleventh aspect, wherein the measurement setting application (224) and the analysis application (225) installed in the server (220) are of Servlet type, a setting method is of wizard type, and data storage is of data base type.

According to a twenty-second aspect of the present invention, in order to achieve the above-described object, there is provided the taste recognition system according to the eleventh aspect, wherein measurement procedure by the measurement setting application (224) includes sensor post-processing, cleaning determination and sensor processing in that order, the sensor post-processing is executed in such a manner that in order to remove substances attached to surfaces of the lipid molecular films (101p) on the sensor probes (101j) of the sensor unit (215) due to previous measurement, the sensor probes (101j) are moved into and out of a plurality of different cleaning solutions (post-processing solutions) an appropriate number of times thereby to execute cleaning process, the cleaning determination is carried out in such a manner that in order to determine the quality of the cleaning process by the sensor post-processing, a result of the cleaning process is measured for each of the plurality of different cleaning solutions (post-processing solutions) used in the sensor post-processing, and the present taste measurement is executed in the sensor processing.

According to a twenty-third aspect of the present invention, in order to achieve the above-described object, there is provided the taste recognition system according to the twelfth aspect, wherein data being measured for taste recognition by the sensor unit (215) are displayed as transient response data on the touch panel (211), and displaying of the transient response data can be confirmed also by the management terminal (227) through the server (220).

According to a twenty-fourth aspect of the present invention, in order to achieve the above-described object, there is provided the taste recognition system according to the thirteenth aspect, wherein in the case where a plurality of taste sensor devices (210, 210, . . . ) with lipid molecular films are connected to a single of the server (220) as a plurality of taste recognition apparatuses, displaying of all the transient response data being measured by the plurality of taste sensor devices (210, 210, . . . ) with lipid molecular films as the plurality of taste recognition apparatuses can be confirmed on the part of the management terminal (227) through the server (220).

According to a twenty-fifth aspect of the present invention, in order to achieve the above-described object, there is provided the taste recognition system according to the eleventh aspect, wherein the analysis application (225) includes a data retrieval function unit (251), a data select function unit (252), a clip board function unit (253), an attenuation ratio of CPA value calculation function unit (254), a quality determining function unit (255), a data export function unit (256), an estimated value calculation function unit (257), a multiple regression analysis function unit (258), a graph overall function unit (259), a history function unit (2510), a basic characteristic analysis unit (2511) and an initialization function unit (2512).

In keeping with the demand to solve the problems of the background art described above, the taste recognition apparatus and the taste recognition system having the aforementioned configuration can be implemented, also to secure a high maintainability, by using a taste sensor device with lipid molecular films and a taste sensing system employing a technique for facilitating both the taste measurement of a sample taste substance as a whole with a simpler operation and the analysis and evaluation of the result of the taste measurement.

BRIEF DESCRIPTION OF DRAWINGS

FIG. 10 is a diagram shown for explaining a screen for selecting a place to store the measurement conditions in FIG. 8.

FIG. 12 is a diagram shown for explaining a screen of the result of multiple regression analysis by a multiple regression analysis function unit 258 attached to the analysis application 225 for analyzing the measurement result as an example of a case in which a transient response graph display is selected in (3) of FIG. 8.

BEST MODE FOR CARRYING OUT THE INVENTION

A taste recognition apparatus and a taste recognition system using the apparatus according to an embodiment of the invention will be explained below with reference to the drawings.

Figure 2:
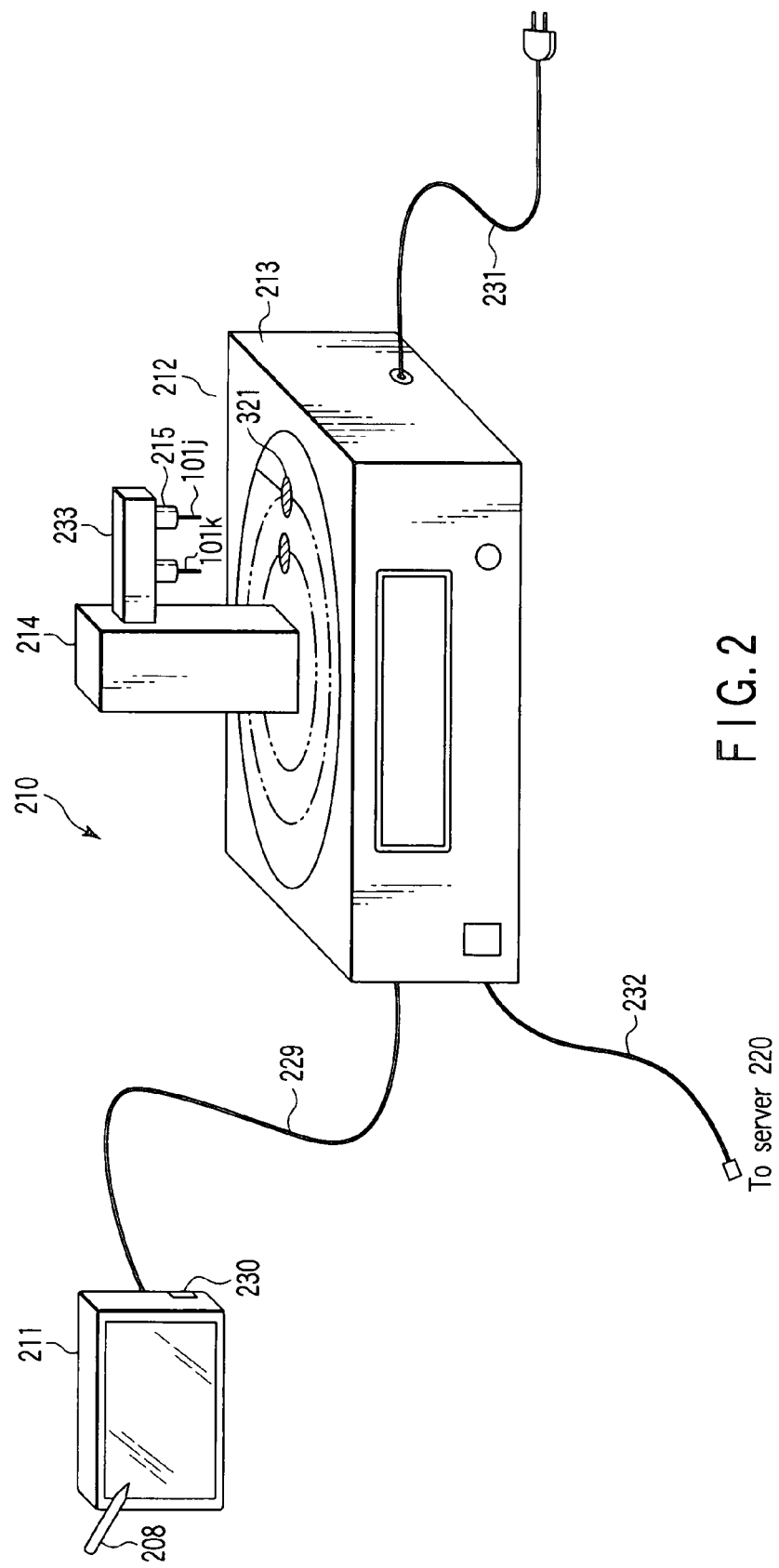
FIG. 2 is a perspective view shown for explaining the configuration of a taste sensor device (device proper) 210 with lipid molecular films and a taste sensing system 200 using the device as a taste recognition apparatus and a taste recognition system using the apparatus according to an embodiment of the invention.

First, an outline of the present invention will be, explained. The taste recognition apparatus according to the invention, as shown in FIG. 2, basically includes: a sensor proper 212 including a sensor unit 215 having sensor probes 101j for measuring a various tastes with lipid molecular films outputting electrical signals presenting taste information much than at least one type of, a solution insertion unit 213 having a plurality of inserting portions 321 arranged at predetermined intervals along the circumference into which a sample taste solution, a standard sample solution and a cleaning solution are selectively inserted, and an arm drive unit 214 for moving the sensor unit 215 with respect to a predetermined inserting portion 321 of the solution insertion unit 213, wherein based on the electrical signal presenting the taste information output from the sensor probes 101j, the measurement for taste recognition of at least the sample taste solution is made possible; and a touch panel 211 so configured that all the operation items required for measurement for taste recognition by the sensor proper 212 are sequentially displayed on a screen as buttons for each function whereby upon designating of a predetermined button by the user, a corresponding one of the operation items can be input so that all the operations of the user on the sensor proper 212 are performed based on displaying on the screen.

Figure 1:
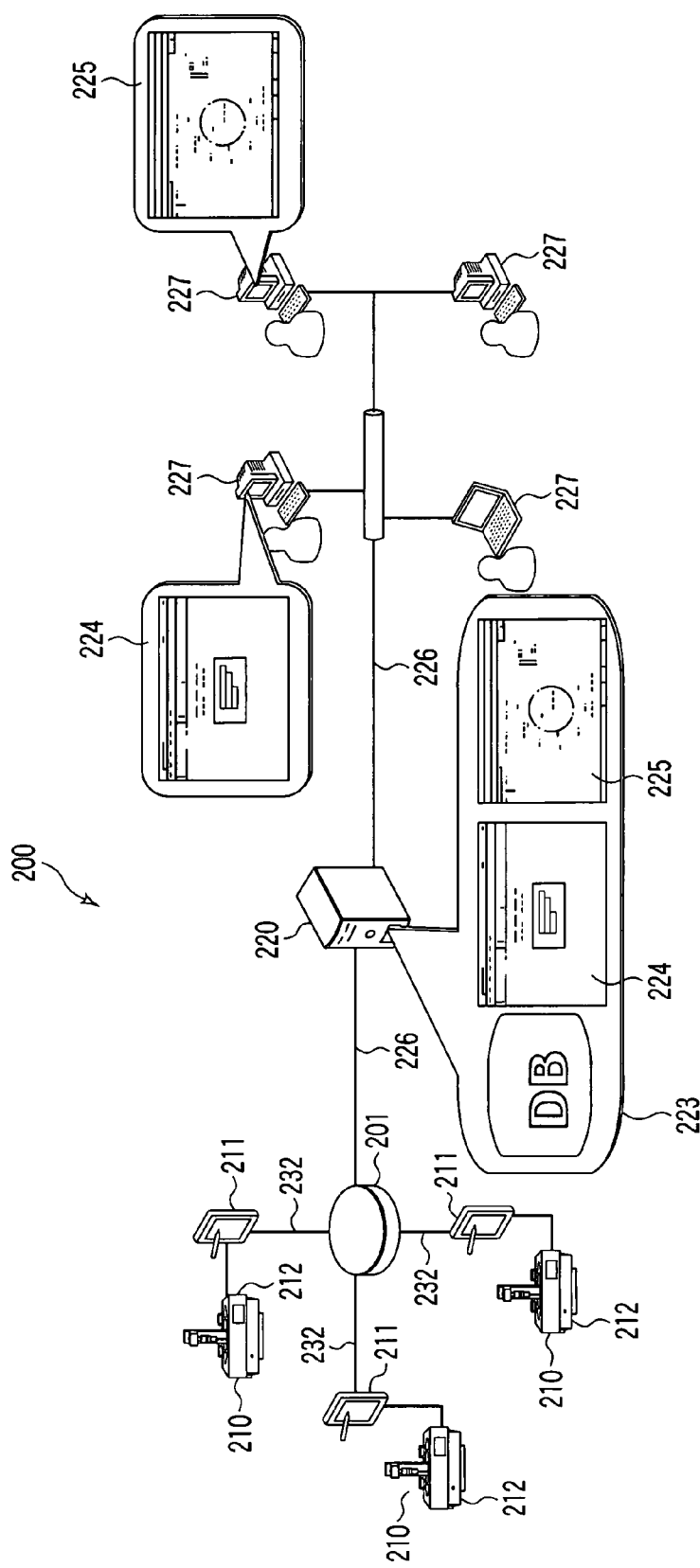
FIG. 1 is a diagram shown for explaining the configuration for connection of a taste sensor device 210 with lipid molecular films and a taste sensing system 200 using the device as a taste recognition apparatus and a taste recognition system using the apparatus according to an embodiment of the invention.

Also, in addition to the configuration of the taste recognition apparatus described above, the taste recognition system according to the invention, as shown in FIG. 1, basically further includes a server 220 having a data base 223 which is installed with a measurement setting application 224 required for measurement for taste recognition by the sensor proper 212 and an analysis application 225 required for analysis of the measurement result for taste recognition by the sensor proper 212 and which has stored therein various data required for the measurement for taste recognition and analysis of the measurement result for taste recognition.

Also, in addition to the configuration of the taste recognition system described above, the taste recognition system according to the invention preferably further includes, as shown in FIG. 1, at least one management terminal 227 for accessing the server 220 through a network 226 and retrieving the measurement setting application 224 and the analysis application 225 installed in the server 220, thereby making it possible to carry out various setting for taste recognition by the sensor proper 212 and analysis of the measurement result for taste recognition.

FIG. 1 is a diagram shown for explaining the configuration for connecting a taste sensor device 210 with lipid molecular films and a taste sensing system 200 using the device as a taste recognition apparatus and a taste recognition system using the apparatus according to an embodiment of the invention.

Specifically, as shown in FIG. 1, the taste sensor device 210 with lipid molecular films and the taste sensing system 200 using the device as a taste recognition apparatus and a taste recognition system using the apparatus according to an embodiment of the invention are so configured that a plurality of taste sensor devices 210 with lipid molecular films can be managed in a centralized way by a single of the server 220 connected through a hub 201.

The server 220 is installed with a data base 223 having stored therein various data as described later, a measurement setting application 224 and an analysis application 225.

A plurality of taste sensor devices 210 with lipid molecular films are configured as a taste recognition apparatus of autonomous control type as described later in accordance with the measurement procedure set by the server 220 or held in advance by each taste sensor device 210. In this way, each taste sensor device 210 with lipid molecular films performs the taste measurement individually, while at the same time outputting each taste measurement result to the server 220 in a serial form as digital data subjected to A/D conversion.

Also, as the measurement procedure set by the server 220, the measurement conditions for the plurality of taste sensor devices 210 with lipid molecular films are set, and the A/D-converted digital data on the taste measurement result sent out from the plurality of taste sensor devices 210 with lipid molecular films are analyzed by accessing the server 220 from a plurality of management terminals 227 connected to the server 220 through the network 226 such as LAN.

Next, there will be explained the configuration of the taste sensor device (hereinafter referred to as the device proper) 210 with lipid molecular films and the taste sensing system 200 using the device as a taste recognition apparatus and a taste recognition system using the apparatus according to an embodiment of the invention.

FIG. 2 is a perspective view shown for explaining the configuration of the taste sensor device (device proper) 210 with lipid molecular films and the taste sensing system 200 using the device as a taste recognition apparatus and a taste recognition system using the apparatus according to an embodiment.

As shown in FIG. 2, the taste sensor device 210 with lipid molecular films and the taste sensing system 200 using the device as a taste recognition apparatus and a taste recognition system using the apparatus according to an embodiment of the invention are configured with a touch panel 211 and a sensor proper 212 connected to each other through a cable 229.

In this case, the sensor proper 212 is connected to a USB connector (host) 230 of the touch panel 211 through a touch panel interface cable 229 about one meter long.

Also, the sensor proper 212 is connected with an AC power cable 231 and a LAN cable 232 leading to the server 220.

In this case, the LAN cable 232 leading to the server 220 may be connected to the touch panel 211 as shown in FIG. 1.

The sensor proper 212 includes, as described in detail later, a solution inserting unit 213, an arm drive unit 214, a sensor unit 215, a plurality of sensor probes 101j and an arm-like sensor board 233.

All the operations of the device proper 210 are performed by an operator touching, i.e. designating, with a touch pen 208 or his/her finger, buttons constituting a selective operation unit sequentially displayed in a wizard form on the touch panel 211 as described later.

Now, the display function of the touch panel 211 will be explained.

The taste recognition apparatus of autonomous control type according to the invention is intended to provide accurate information to the user by displaying setting information and measurement data on a monitor with the touch panel 211 and also to provide a graphic user interface (GUI) whereby every person can operate a taste recognition apparatus easily by receiving only the required input from the user through the touch panel 211 installed on the monitor.

As a display function of the touch panel 211, each function is assigned to a button and only the function required on each occasion is displayed on the screen. Thus, the user, by designating each button in accordance with the contents of each setting on display, can set all the items required for measuring operation of the taste recognition apparatus.

As a result, in the autonomous taste recognition apparatus according to the invention, every user can set the measurement through the touch panel 211 without committing any error. Also, at the time of measurement, the data required for checking the measurement data is displayed on the screen of the touch panel 211, and therefore, the user can constantly confirm the situation of the device proper 210, the sensor unit 215 and the sample to be measured as described later.

Also, in the taste recognition apparatus of autonomous control type according to the invention, as an input function of the touch panel 211, the input from the user is applied from the screen of the touch panel 211 by designating the button displayed on the same screen. By the input from the screen of the touch panel 211, therefore, the user can intuitively perform the operation, while at the same time presenting the display contents to the user on the screen of the touch panel 211 as occasion demands, thereby preventing the user from committing an operating error.

Also, various samples including the sample taste solution and the standard sample solution and the cleaning solution are inserted by the user (hereinafter referred to as the operator) into the solution insertion unit 213 of the sensor proper 212 based on the instruction for arrangement of the cleaning solution and the sample displayed on the touch panel 211 as described later.

As a result of these operations, the taste sensor device 201 with lipid molecular films and the taste sensing system 200 using the device as a taste recognition apparatus and a taste recognition system using the apparatus according to the invention can meet the demand to measure and recognize the taste of a sample taste substance with a simpler operation.

The taste measurement for taste recognition with the sensor proper 212 is carried out by the measurement procedure set by the server 220 as described later or the measurement procedure held in advance by each taste sensor device 210 itself.

In the process, the information on the taste measurement by the sensor proper 212 is displayed on the touch panel 211.

Figure 3A:
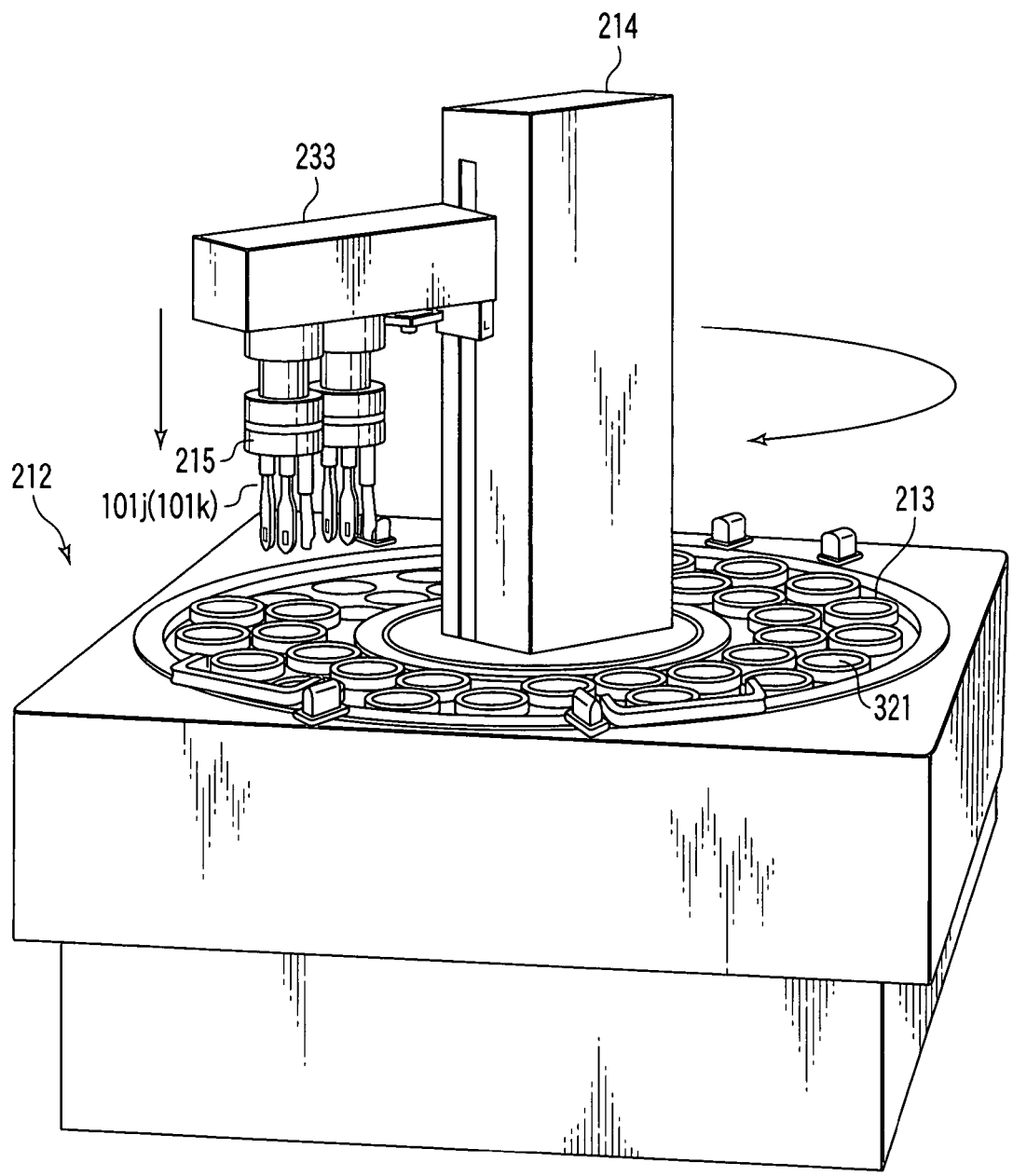
FIG. 3A is a perspective view shown for explaining the outer configuration of the sensor proper 212 of the taste sensor device (device proper) 210 with lipid molecular films and a taste sensing system 200 using the device as the taste recognition apparatus and a taste recognition system using the apparatus according to an embodiment of the invention.

FIG. 3A is a perspective view shown for explaining the outer configuration of the sensor proper 212 of the taste sensor device (device proper) 210 with lipid molecular films and the taste sensing system 200 using the device as a taste recognition apparatus and a taste recognition system using the apparatus according to an embodiment of the invention.

Figure 3B:
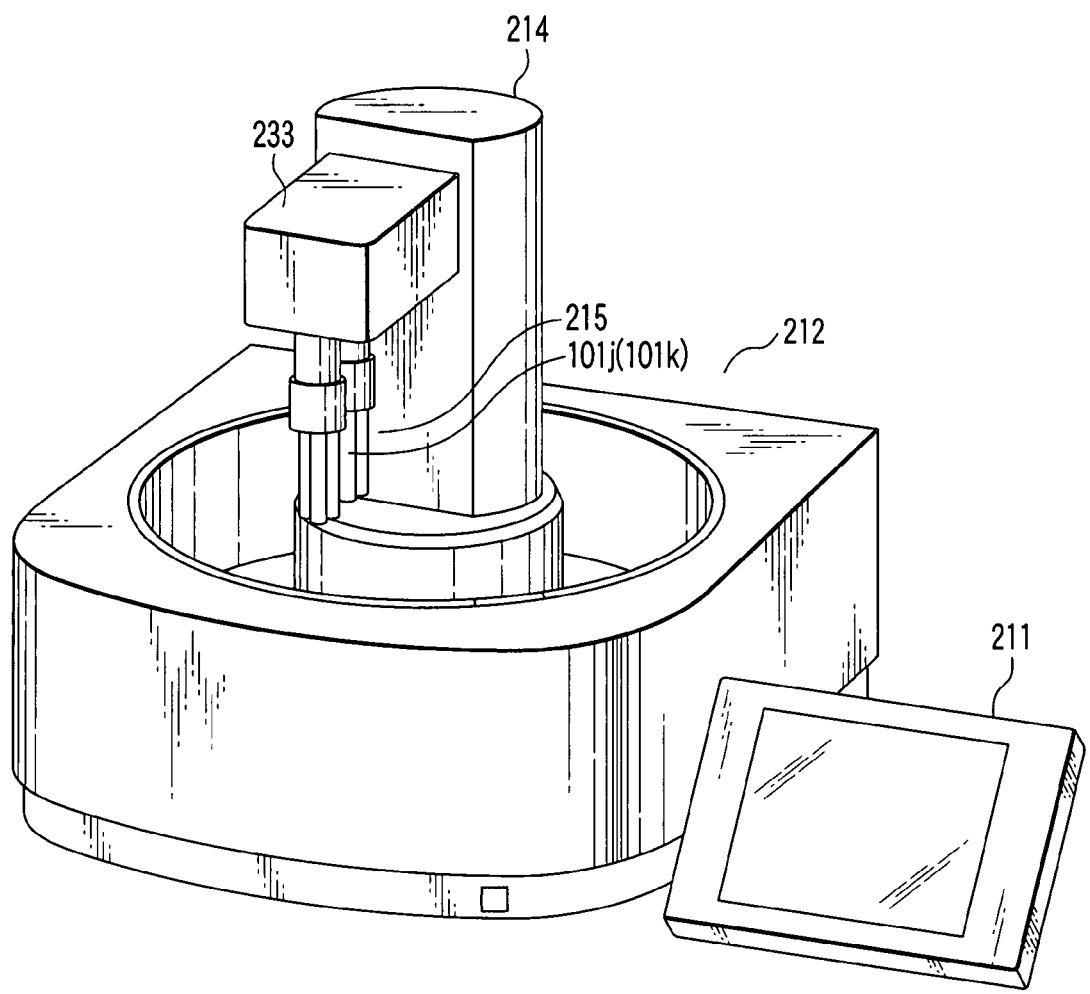
FIG. 3B is a perspective view shown, with a plurality of solution insertion portions 321 of the sensor proper 212 removed, for explaining the outer configuration of the sensor proper 212 and a touch panel 211 of the taste sensor device (device proper) 210 with lipid molecular films and the taste sensing system 200 using the device as a taste recognition apparatus and a taste recognition system using the apparatus according to an embodiment of the invention.

FIG. 3B is a perspective view shown, with the solution insertion portion 321 of the sensor proper 212 removed, for explaining the outer configuration of the sensor proper 212 and the touch panel 211 of the taste sensor device proper (device proper) 210 with lipid molecular films and the taste sensing system 200 using the device as a taste recognition apparatus and a taste recognition system using the apparatus according to an embodiment of the invention.

As shown in FIGS. 3A, 3B, the sensor proper 212 includes the aforementioned solution insertion unit 213 (not shown in FIG. 3B), the arm drive unit 214, the sensor unit 215, a plurality of the sensor probes 101j and the arm-like sensor board 233.

Figure 4:
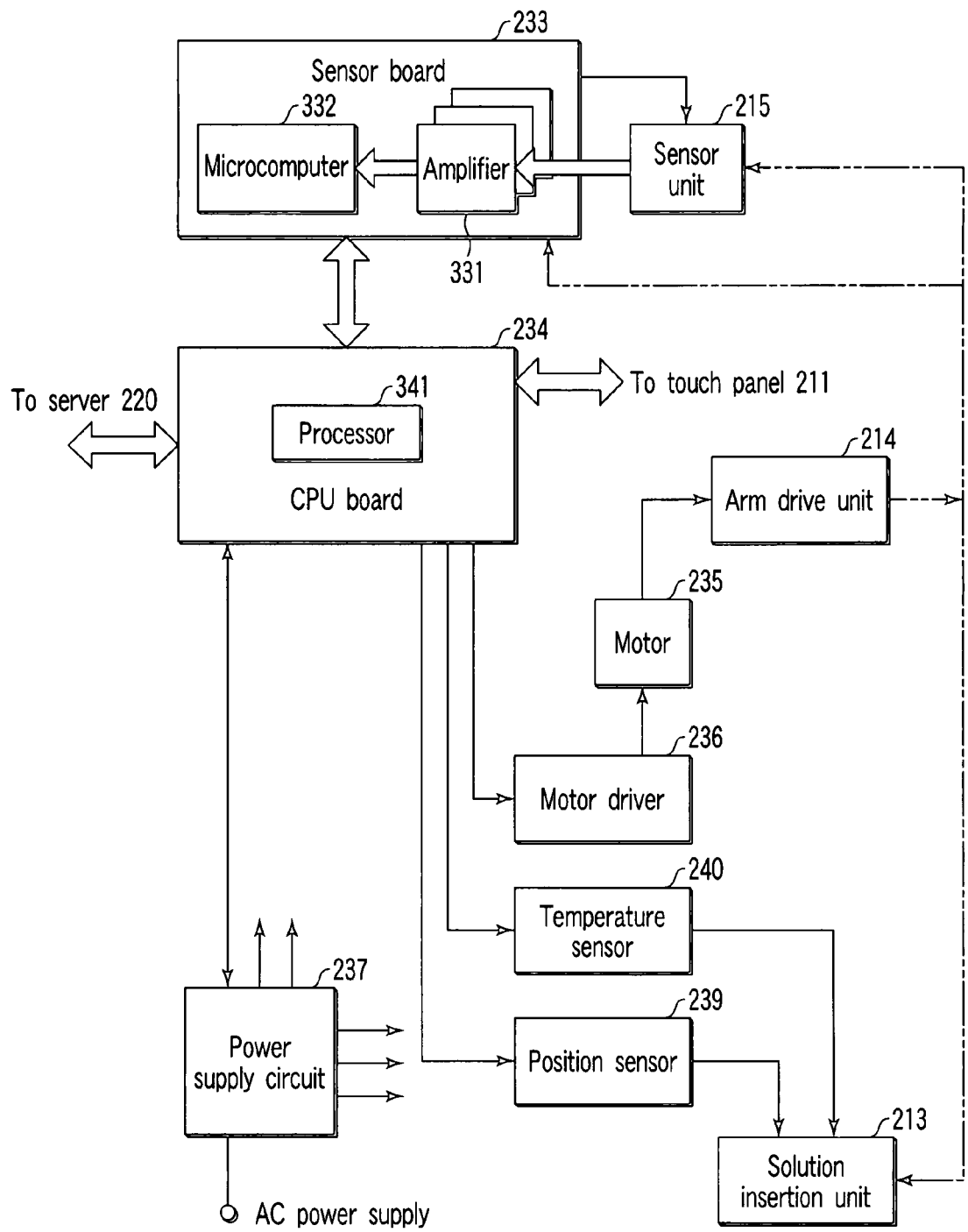
FIG. 4 is a diagram shown for explaining the internal configuration of the sensor proper 212 of the taste sensor device 210 with lipid molecular films and the taste sensing system 200 using the device as a taste recognition apparatus and a taste recognition system using the apparatus according to an embodiment of the invention.

FIG. 4 is a diagram shown for explaining the internal configuration of the sensor proper 212 of the device proper 210 in the taste sensor device 210 with lipid molecular films and the taste sensing system 200 using the device as a taste recognition apparatus and a taste recognition system using the apparatus according to an embodiment of the invention.

As shown in FIG. 4, the sensor proper 212, in addition to the aforementioned arm-like sensor board 233, includes a CPU board 234, a motor 235, a motor driver 236, a power supply circuit 237, a position sensor 239 and a temperature sensor 240.

The power supply circuit 237 is a circuit for supplying a predetermined DC drive voltage or a predetermined AC drive voltage to each part of the sensor unit 212 based on the AC voltage supplied from the AC power supply cable 31 shown in FIG. 2.

As shown in FIG. 3A, the solution insertion unit 213 has a plurality of inserting portions 321 arranged at predetermined intervals on the circumference. As described above, the various samples including the sample taste solution and the standard sample solution and the cleaning solution are inserted by the operator into the plurality of inserting portions 321 based on the instruction for arrangement of the samples and the cleaning solution for solution insertion displayed on the screen of the touch panel 211 as described later.

At the central part of the solution insertion unit 213, the arm drive unit 214 is arranged upright. The arm-like sensor board 233 is arranged on the part of the arm drive unit 214 extending horizontally from the upper portion thereof.

With this arm drive unit 214, the sensor unit 215 supported at the forward end portion of the arm-like sensor board 233 is rotationally moved along the circumference by the motor 235 controlled by the motor driver 236 and located at the desired inserting portion 321 of the solution insertion unit 213. At the same time, with the sensor unit 215 located at the desired inserting portion 321, the sensor unit 215 is slid vertically so that the plurality (for example, 8 channels) of sensor probes 101j of the sensor unit 215 and the reference electrode 101k are driven and dipped by being repeatedly moved into and out of the sample taste solution, the reference sample solution and the cleaning solution inserted into the desired inserting portion 321.

At the lower part of the forward end of the arm-like sensor board 233, the sensor unit 215 is supported rotatably in the circumferential direction of the solution insertion unit 213 by the arm (drive unit) 214 on the one hand, and the plurality of (for example, 8 channels) sensor probes 101j of the sensor unit 215 are vertically supported movably on a predetermined one of the plurality of inserting portions 321 on the other hand.

Figure 23:
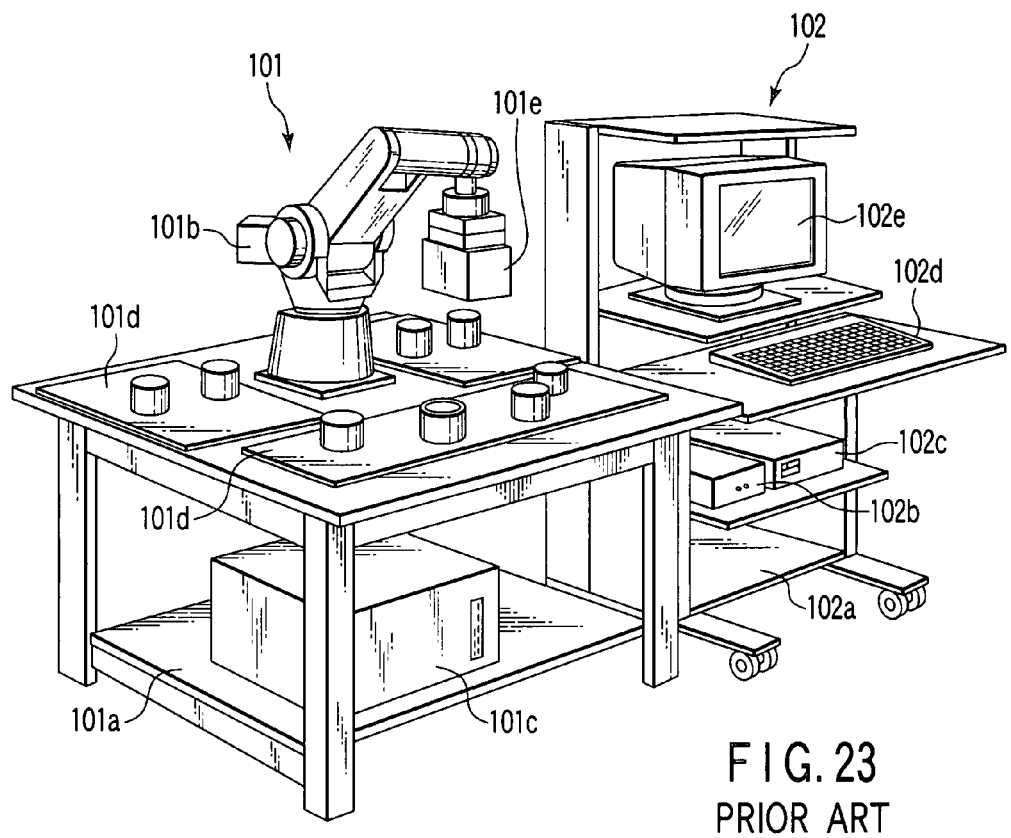
FIG. 23 is a perspective view shown for explaining the configuration of a batch-type taste recognition system disclosed in Patent Document 4 as a conventional taste recognition apparatus.
Figure 24:
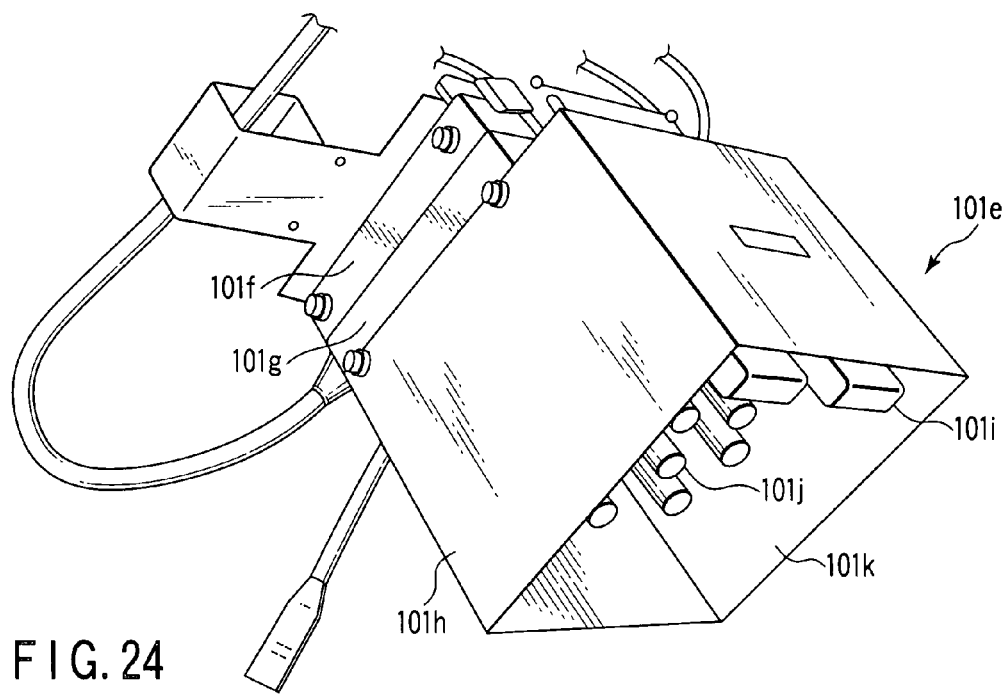
FIG. 24 is a perspective view shown for explaining the configuration of a sensor unit 101e of the batch-type taste recognition system disclosed in Patent Document 4 as a conventional taste recognition apparatus.

The sensor 215, like the sensor unit 101e disclosed in Patent Document 4 shown in FIG. 23, for example, includes a plurality of (for example, 8-channel) sensor probes 101j and the reference electrode 101k as shown in FIG. 24.

Figure 25A:
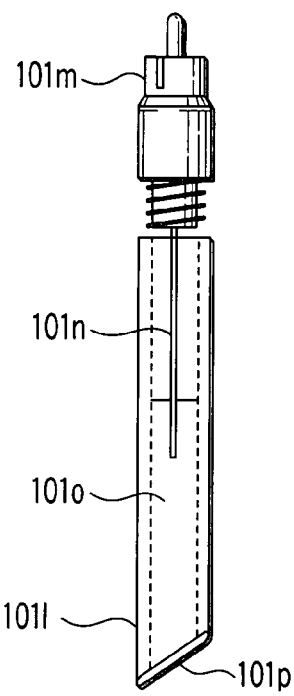
FIG. 25A is a side view shown for explaining the configuration of one of sensor probes 101j of the sensor unit 101e in the batch-type taste recognition system disclosed in Patent Document 4 as a conventional taste recognition apparatus.
Figure 25B:
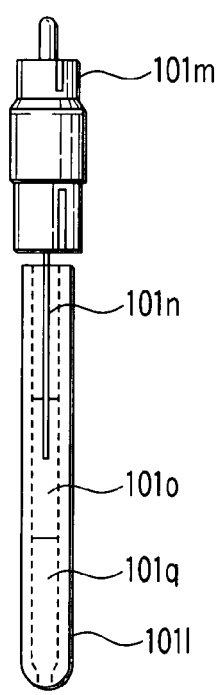
FIG. 25B is a side view shown for explaining the configuration of a reference electrode 101k of the sensor unit 101e in the batch-type taste recognition system disclosed in Patent Document 4 as a conventional taste recognition apparatus.
Figure 26:
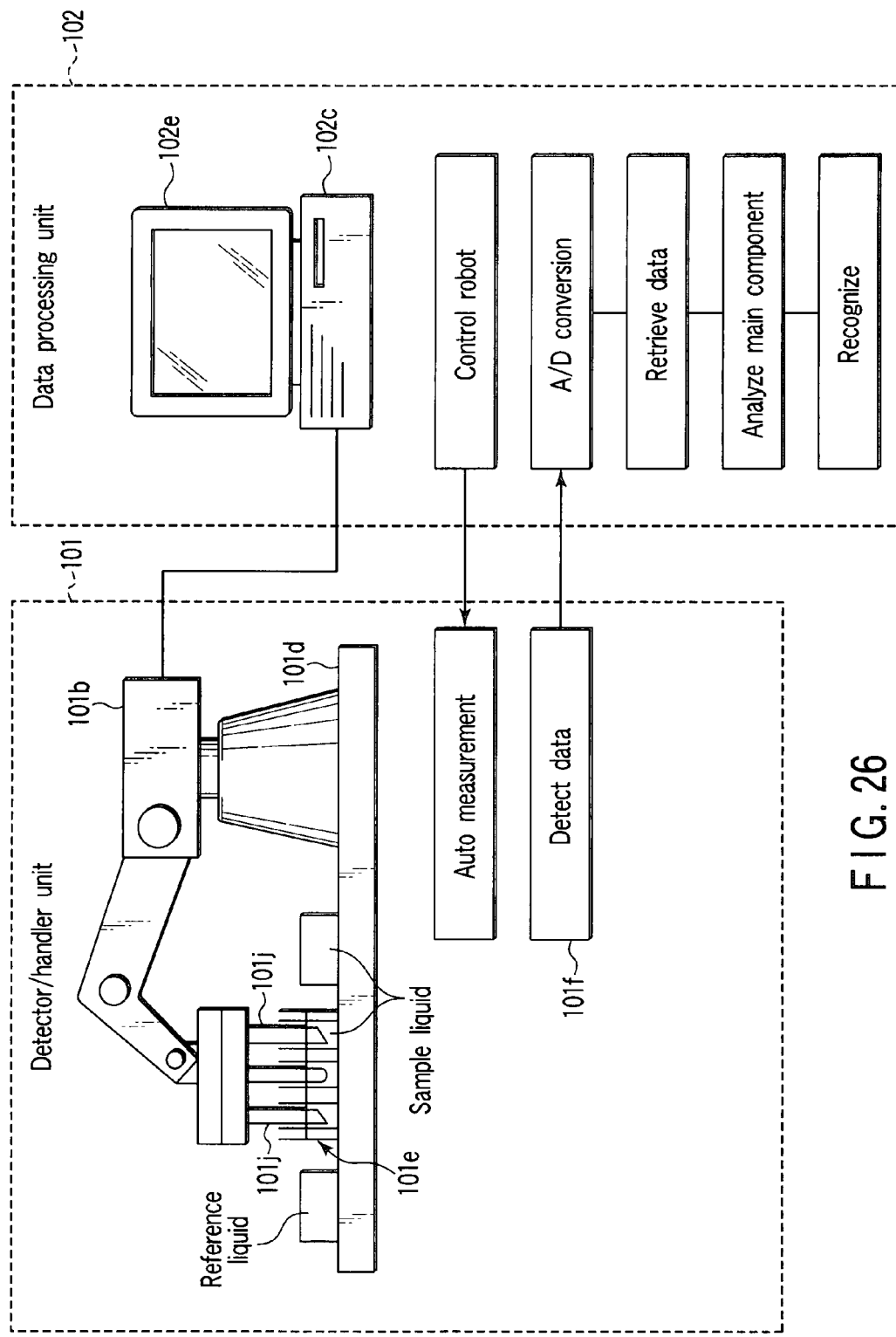
FIG. 26 is a block diagram shown for explaining the configuration of a control system of the batch-type taste recognition system disclosed in Patent Document 4 as a conventional taste recognition apparatus.
Figure 27A:
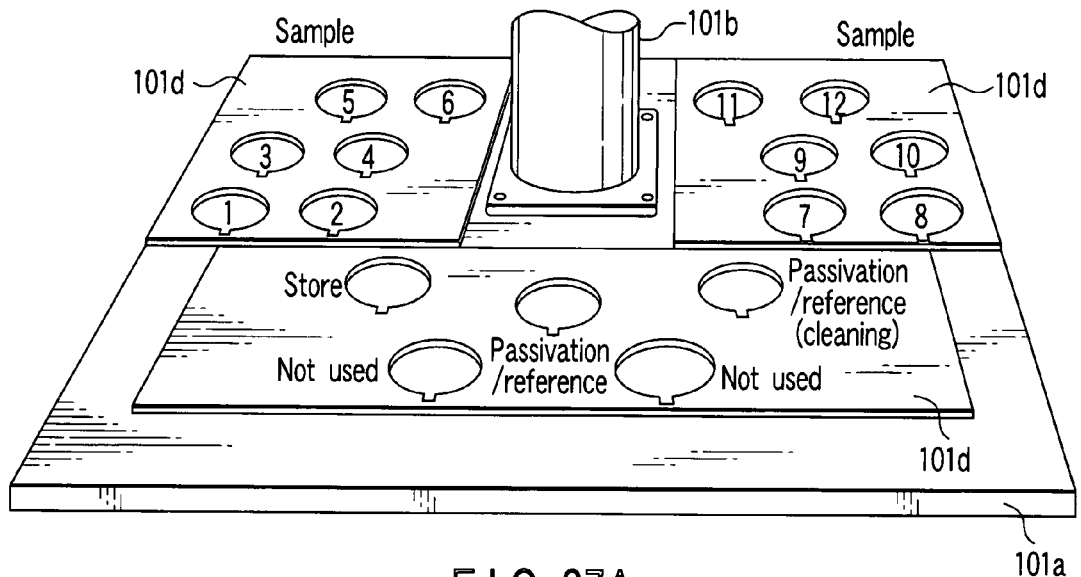
FIG. 27A is a perspective view shown for explaining automatic measurement carried out by dipping the sensor unit 101e in a reference liquid container, a stabilization solution container, a cleanser container, a measurement liquid (sample liquid) container, etc. mounted in a predetermined form on a container mounting plate 101d of the batch-type taste recognition system disclosed in Patent Document 4 as a conventional taste recognition apparatus.
Figure 27B:
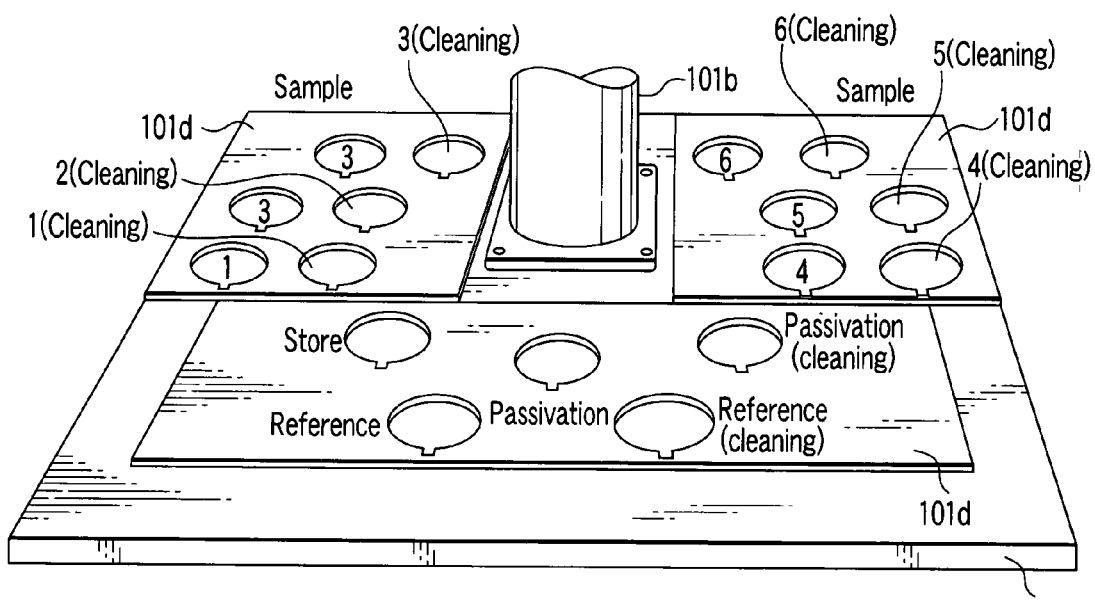
FIG. 27B is a perspective view shown for explaining the automatic measurement carried out by dipping the sensor unit 101e in the reference liquid container, the stabilization liquid container, the cleanser container, the measurement liquid (sample liquid container, etc. mounted in a predetermined form on the container mounting plate 101d of the batch-type taste recognition system disclosed in Patent Document 4 as a conventional taste recognition apparatus.

The sensor probes 101j and the reference electrode 101k, as disclosed in Patent Document 4 shown in FIGS. 25A, 25B, each include a probe proper 101l, an electrode terminal 101m, an Ag/AgCl electrode 101n and an internal liquid (saturated AgCl, 3.3 MKCl) 101o. Also, a lipid substance film 101p is arranged at the forward end of the sensor probes 101j.

Incidentally, the position sensor 239 is arranged on the sensor unit 215 or the like, and detects whether the sensor unit 215 is located at an intended inserting portion 321 of the plurality of solution insertion units 213.

Also, the temperature sensor 240 is arranged on the sensor unit 215 or the like, and detects whether the temperature of the sample taste solution, the standard sample solution and the cleaning solution is in a predetermined range (for example, between 20 and 40° C.) or not.

The plurality (for example, 8 channels) of sensor probes 101j of the sensor unit 215 and the reference electrode 101k are connected to the electrical circuit portion of the arm-like sensor board 233 to supply a predetermined voltage to the plurality of sensor probes 101j and the reference electrode 101k, while at the same time outputting the potential difference of the plurality of channels generated by dipping the plurality of sensor probes 101j in the sample taste solution and the standard sample solution inserted into the inserting portion 321.

The potential difference of the plurality of channels are subjected to A/D conversion by being fetched into the microcomputer 332 through the amplifier 331 arranged in the electrical circuit portion of the arm-like sensor board 233 as an electrical signal presenting the taste information of the sample taste solution and the standard sample solution.

The digital data presenting the taste information subjected to A/D conversion by the microcomputer 332 can be sent out to the CPU board 234 by way of as few wires as possible in a serial form.

The digital data presenting the taste information are sent out to the server 220 through the CPU board 234.

In this case, if the analog electrical signals presenting the taste information before A/D conversion are sent out in parallel to the CPU board 234 from the arm-like sensor board 233 so as to perform A/D conversion at the CPU board 234, as many wires as the plurality of (for example 8-channel) sensor probes 101j and the reference electrode 101k would be required between the arm-like sensor board 233 and the CPU board 234, resulting in excessively many wires arranged between the sensor board and the CPU board provided in the arm drive unit 214.

As a result, mechanical rotational movement with the arm drive unit 214 may encounter a trouble. It is very important, therefore, to send out the electrical signal to the CPU board 234 through as few wires as possible as described above.

A processor 341 mounted on the CPU board 234 takes charge of control of the sensor proper 212 as a whole.

The CPU board 234 sends and receives predetermined data and signals to and from the touch panel 211 making up the device proper 210 with the sensor proper 212.

Next, the functions accompanying the device proper 210 will be explained.

First, the processor 341 mounted on the CPU board 234 of the device proper 210 is a kind of the microprocessor with Linux built in as OS, or for example, an SH3 processor of autonomous control type, as described above, available from Hitachi Information & Control Solutions, Ltd.

As a result, the device proper 210 has no built-in control functions other than measurement, and therefore, no other functions are accessed during measurement operation. Thus, the measurement operation is not unduly suspended, and a constantly stable operation is secured.

The display by the touch panel 211 is the graphic user interface (GUI) of the wizard type described above, based on Xwindow (registered trademark).

All the operations of the operator on the device proper 210 are performed based on the display, described later, by the touch panel 211 as described above.

The taste measurement carried out by the sensor unit 215 of the device proper 210 includes a normal measurement mode, a maintenance measurement mode carried out before the normal measurement mode and a sensor check mode carried out before the maintenance measurement mode.

The sensor check mode is carried out to confirm whether the taste measurement is properly conducted by the sensor unit 215 of the device proper 210.

Once the proper taste measurement carried out by the sensor unit 215 of the device proper 210 is confirmed by execution of the sensor check mode, mode control proceeds to the normal measurement mode.

In the case of "NG" confirming that the proper taste measurement cannot be carried out by the sensor unit 215 of the device proper 210 in the execution of the sensor check mode, the mode control proceeds to the maintenance measurement mode.

In the maintenance measurement mode, a basic measurement of the standard sample solution and a basic measurement analysis for analyzing the result of the basic measurement are carried out, and based on the result of this analysis, necessary measures such as cleaning described later is carried out, followed by the sensor check mode again.

Gain and offset calibration of the amplifier 331 arranged in the electrical circuit portion of the arm-like sensor board 233 of the device proper 210 is carried out automatically by initialization.

The processor 341 mounted on the CPU board 234 of the device proper 210 semiautomatically (automatically for calculation) carries out calibration of the temperature sensor 240 arranged in the sensor unit 215 of the device proper 210.

Also, the processor 341 mounted on the CPU board 234 of the device proper 210 semiautomatically (position information is updated automatically) carries out position adjustment with the position sensor 239 arranged in the sensor unit 215 of the device proper 210.

By these operations, the taste sensor 210 with lipid molecular films and the taste sensing system 200 using the sensor as a taste recognition apparatus and a taste recognition system using the apparatus according to an embodiment of the invention have the maintainability of each part improved, thereby making it possible to meet the demand for a better maintainability.

Also, the processor 341 mounted on the CPU board 234 of the device proper 210 has a self-diagnosis function of not only hardware check including periodic confirmation of a trouble of the electrical circuit portion, etc. of the sensor board 233 of the device proper 210 and connection/disconnection of the wires of each part but also the check of the sensor unit 215 by constantly monitoring the anomaly of the measurement value (drop-off value), and based on the result of these checks, detecting a trouble, if any, of each part and identifying a trouble point.

Specifically, according to the invention, the processor 341 mounted on the CPU board 234 has the self-diagnosis function of the hardware check including the periodic confirmation of any trouble of the electrical circuit portion of the arm-like sensor board 233 of the device proper 210 and the connection/disconnection of the wires of each part and/or monitoring of any trouble of the measurement result of the sensor unit 215.

The processor 341 mounted on the CPU board 234 of the device proper 210, having the self-diagnosis function described above, prompts the operator to conduct the required maintenance work by issuing an alarm to indicate the trouble point on the touch panel 211, for example, upon detection of a trouble of any part of the device proper 210.

As a result, the taste sensor 210 with lipid molecular films and the taste sensing system 200 using the taste sensor 210 as a taste recognition apparatus and a taste recognition system using the apparatus according to an embodiment of the invention, having the function of self-diagnosing each part of the device proper 210, can meet the demand to facilitate the grasping of the trouble point and the solution thereof at the time of occurrence of a trouble.

Also, the processor 341 mounted on the CPU board 234 of the device proper 210 has stored therein a plurality of measurement patterns including the measurement procedure prepared as an autonomous control type described above, and with the device proper 210 alone, can measure the taste while at the same time dealing with a remote access from an external host device including the server 220.

Also, the processor 341 mounted on the CPU board 234 of the device proper 210, adapted for a network, makes possible the centralized management of the measurement data of a plurality of devices proper 210 with a single of the server 220.

Incidentally, as a level of the user of the device proper 210, two levels including the administrator and the user can be involved.

Next, there will be explained the configuration of the server 220 in the taste sensor device 210 with lipid molecular films and the taste sensing system 200 using the device as a taste recognition apparatus and a taste recognition system using the apparatus according to an embodiment of the invention.

Figure 5:
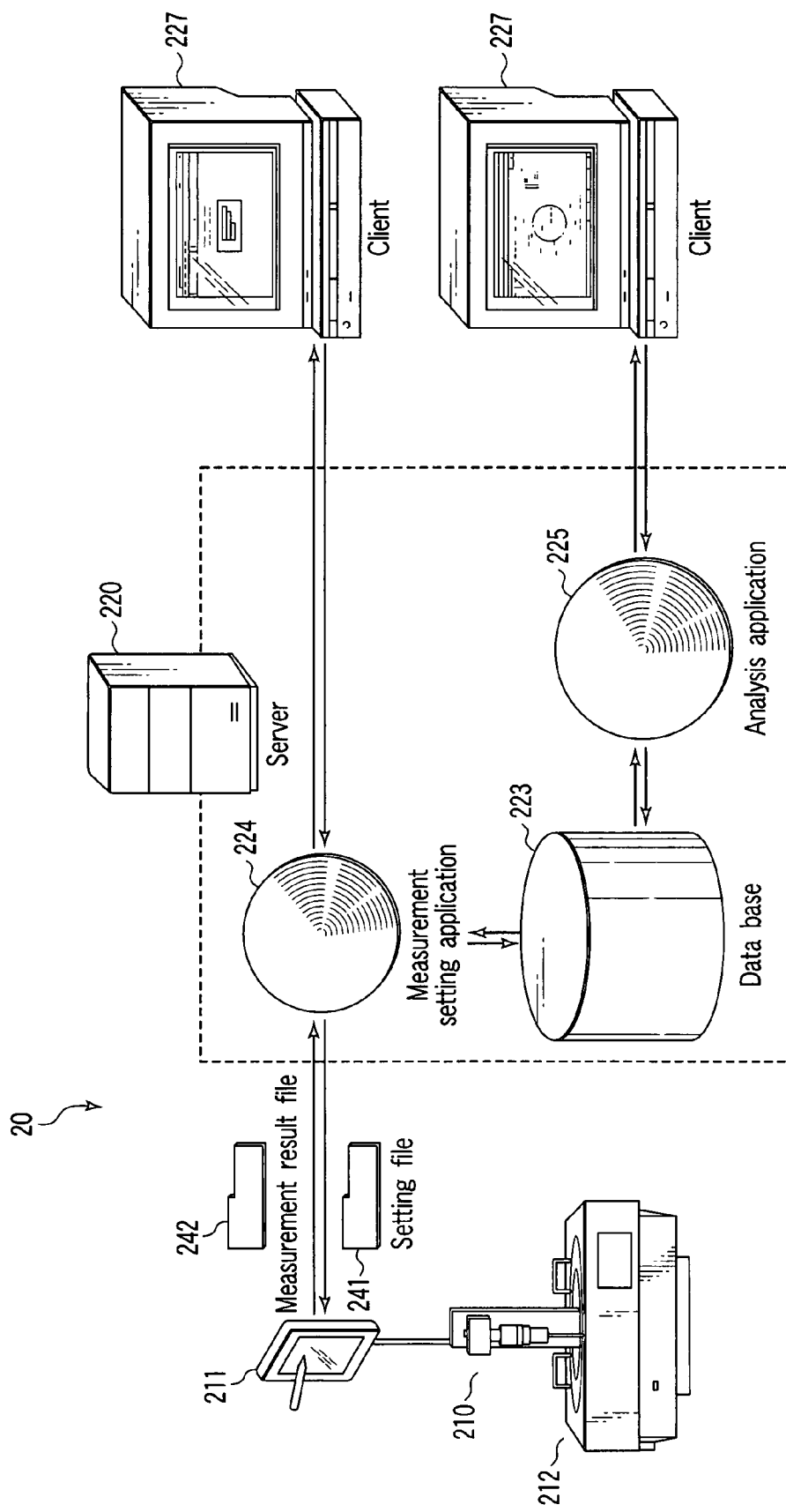
FIG. 5 is a diagram shown for explaining the configuration of a server 220 of the taste sensor device 210 with lipid molecular films and the taste sensing system 200 using the device as a taste recognition apparatus and a taste recognition system using the apparatus according to an embodiment of the invention.

FIG. 5 is a diagram shown for explaining the configuration of the server 220 in the taste sensor device 210 with lipid molecular films and the taste sensing system 200 using the device as a taste recognition apparatus and a taste recognition system using the apparatus according to an embodiment of the invention.

Specifically, as shown in FIG. 5, the server 220 in the taste sensor device 210 with lipid molecular films and the taste sensing system 200 using the device according to the invention has a data base 223 as described above, and has installed therein the measurement setting application 224 for taste recognition and the analysis application 225.

The data base 223 has stored therein all the data handled in the taste sensor device 210 with lipid molecular films and the taste sensing system 200 using the device, including the various setting data such as the various data required for measurement for taste recognition and the various data required for analysis of the measurement result for taste recognition, the measurement result data and the analysis procedure data.

Also, the measurement setting application 224 has installed therein the application for measurement setting for taste recognition.

The analysis application 225, on the other hand, has installed therein an application for analysis of the measurement result of taste recognition.

The server 220 is accessed by the client (terminal 227) and the application for measurement setting for taste recognition installed in the measurement setting application 224 is retrieved thereby to permit the sensor unit 215 of the device proper 210 to make various settings for taste measurement.

Specifically, as shown in FIG. 5, a setting file 241 is sent to the device proper 210 from the measurement setting application 224 of the server 220, while at the same time a measurement result file 242 is sent from the device proper 210 to the measurement setting application 224 of the server 220.

The measurement result file 242 sent to the measurement setting application 224 of the server 220 from the device proper 210 is stored in the data base 223 of the server 220.

Also, the server 220 is accessed by the client (terminal 227) and the application 225 for measurement result analysis installed in the analysis application 225 of the server 220 is retrieved. At the same time, by accessing the measurement result file 242 stored in the data base 223 of the server 220, the taste measurement result is analyzed by the sensor unit 215 of the device proper 210 on the part of the client (terminal 227).

The client (terminal 227) accessing the server 220 can be a personal computer (PC) of any model of Windows (registered trademark) as OS installed with Internet Explorer 6.0.

As described above, the taste sensing system 200 using the taste sensor device 210 with lipid molecular films as a taste recognition apparatus and a taste recognition system using the apparatus according to an embodiment of the invention assumes a form to access and use the application 224 for measurement setting and the application 225 for measurement result analysis installed in the server 220, and therefore, these applications are not required to be installed in the client (terminal 227) beforehand.

As a result, the taste sensing system 200 using the taste sensor device 210 with lipid molecular films as a taste recognition apparatus and a taste recognition system using the apparatus according to an embodiment of the invention can meet the demand to eliminate the need of correcting the software of the taste sensing system with lipid molecular films regardless of any version-up of the OS of the personal computer used as a terminal.

Next, the functions attached to the server 220 will be explained.

The OS of the processor built in the server 220 is Linux, each application is Servlet in format, the setting method is of wizard type, and the data is held in a data base.

Incidentally, the two user levels including the administrator and the user in general are set for the server 220 as in the case of the device proper 210.

The measurement procedure set in the device proper 210 from the server 220 as described above includes the sensor post-processing, cleaning determination and the sensor processing, in that order, by the measurement setting application 224 of the server 220.

The sensor post-processing is defined as a process in which in order to remove a substance attached to the surface of the lipid molecular film 101*p* in the sensor probes 101*j* of the sensor unit 215 by the previous measurement, the sensor probes 101*j* are cleaned by being moved into and out of a plurality of different cleaning solutions (post-processing solution) an appropriate number of times, followed by measurement again.

Also, the cleaning determination is defined as a process of determining the quality of the cleaning process by the sensor post-processing, and a CPA (change of membrane potential caused by adsorption) value obtained as a result of the cleaning process is measured for each of a plurality of (for example, 2 to 5) different types of the cleaning solution (post-processing solution) used in the sensor post-processing.

Also, the sensor processing is defined as the present process executed to measure the taste.

All the measurement result data are held in the data base 223 of the server 220.

In this case, all the transient response measurement values including all the sample values obtained at intervals of one second, for example, are recorded with an electronic signature in the form prohibiting the alteration.

Also, the transient response data in measurement are displayed on the touch panel 211 of the device proper 210 as described above, and the display of the particular transient response data can be confirmed also on the part of the client (terminal 227) through the server 220.

These operations of recording and confirmation of the measurement result data can check whether the measurement result data has developed an abnormal value or not as a part of the self-diagnosis function described above, while at the same time making it possible to check whether the measurement result data, i.e. variation of the taste of the sample taste solution itself has occurred or not.

In the case where a plurality of devices proper 210 are connected to the server 220, the display of all the transient response data being measured by the plurality of devices proper 210 can be confirmed on the part of the client (terminal 227) through the server 220.

Also, the server 220 can take the required measure against the remote access from an external host device.

Also, the taste recognition system according to the invention can be provided with a network, so that the measurement data derived from the plurality of devices proper 210 can be centrally managed by a single server 220.

Next, the functions attached to the analysis application 225 for measurement result analysis will be explained.

Figure 6A:
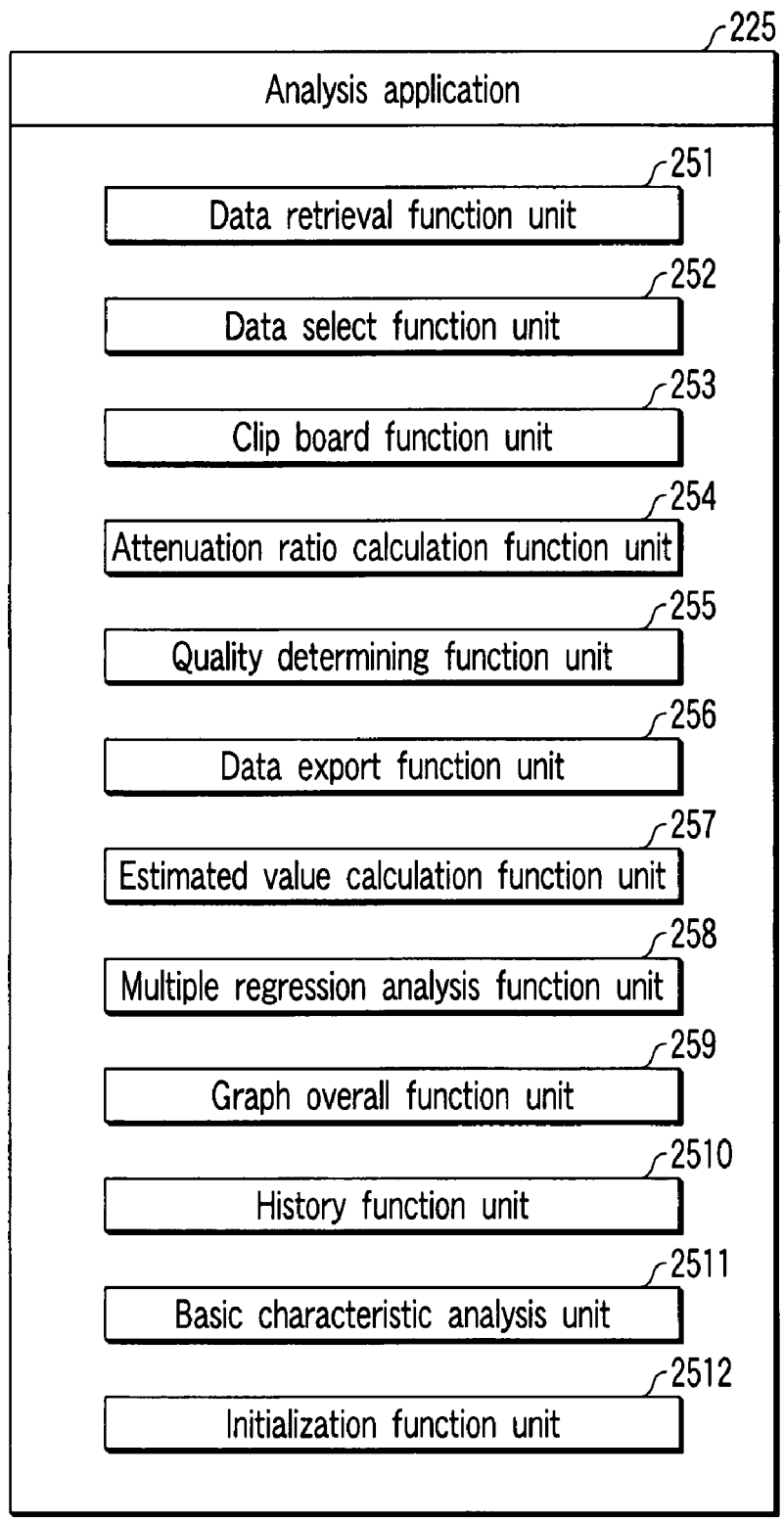
FIG. 6A is a function block diagram shown for explaining functions accompanying an analysis application 225 for analyzing the measurement result installed in the server 220.

FIG. 6A is a function block diagram shown for explaining the functions attached to the analysis application 225 for analysis of the measurement result.

Specifically, as shown in FIG. 6A, the analysis application 225 for analysis of the measurement result includes a data retrieval function unit 251, a data select function unit 252, a clip board function unit 253, an attenuation ratio calculation function unit 254, a quality determining function unit 255, a data export function unit 256, an estimated value calculation function unit 257, a multiple regression analysis function unit 258, a graph overall function unit 259, a history function unit 2510, a basic characteristic analysis unit 2511 and an initialization function unit 2512.

The data retrieval function unit 251 has the function of retrieving the data stored in the data base 223.

Also, the data select function unit 252 has the function of rearranging the data while at the same time selecting the data used for analysis.

The clip board function unit 253 has the function of storing a maximum of 20 data sets used for data coupling.

Also, the attenuation ratio of CPA value calculation function unit 254 has the function of calculating the attenuation ratio by RCPA1.

The attenuation ratio of CPA value calculation is a function of evaluating the durability of the after-taste by measuring the after-taste (CPA value) by repeating the sensor post-processing described above and calculating the percent based on the first CPA value.

Also, RCPA is an abbreviation of "ratio of CPA", and can be calculated by the calculation formula:

$$RCPA(N) = CPA(N) \times 100\% / CPA1.$$

By this attenuation ratio calculation, the sustainability of bitterness of a medicine as a sample or "crispness" of beer as a sample can be evaluated.

Figure 6B:
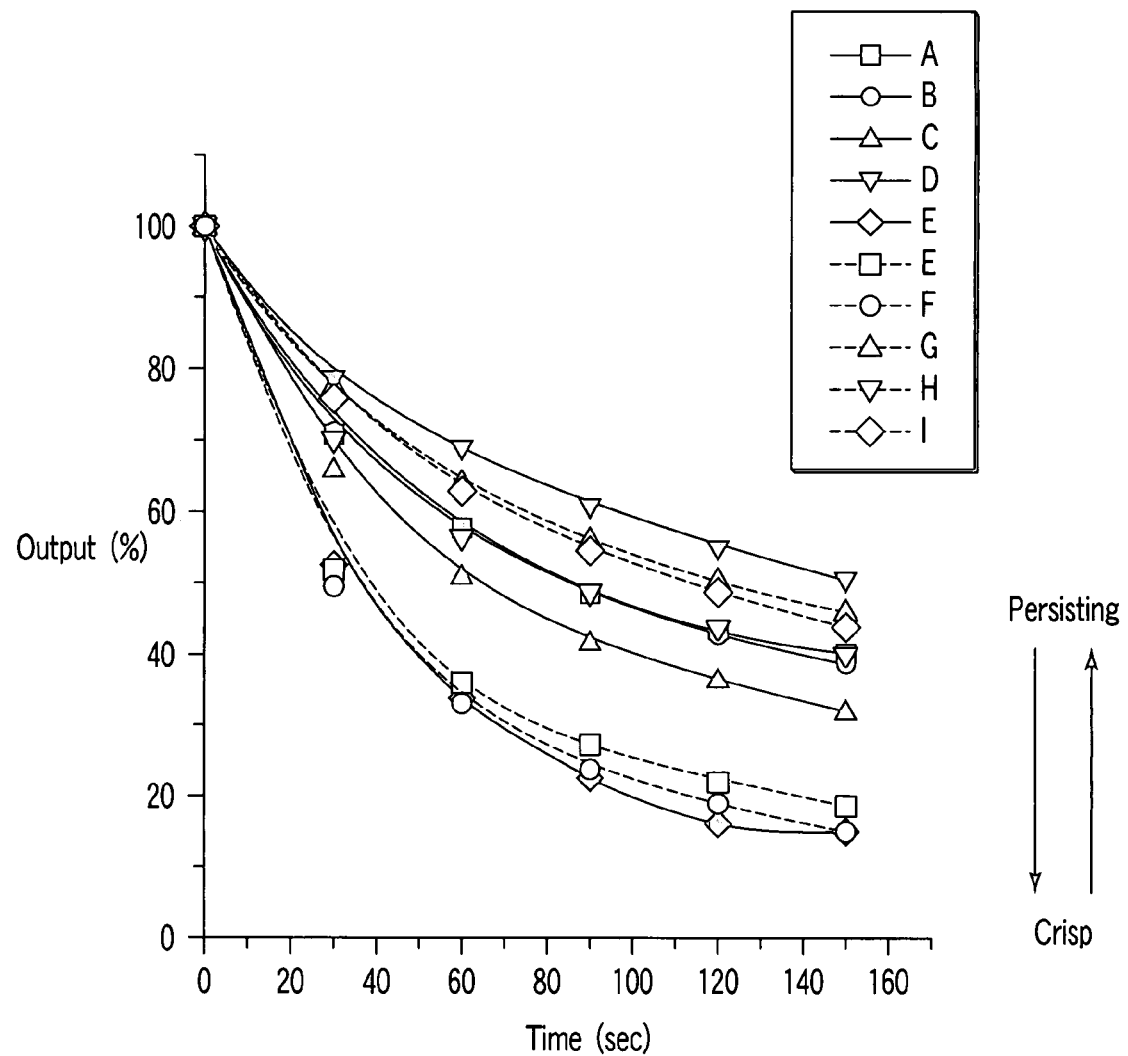
FIG. 6B is a characteristic diagram shown for explaining an example of observation of after-taste progress with time using the result of attenuation ratio calculation about samples A to I by an attenuation ratio of CPA value calculation function 254 attached to the analysis application 225 for analyzing the measurement result installed in the server 220.

FIG. 6B shows an example of observation of the after-taste with time using the result of the attenuation ratio of CPA value calculation for the samples A to I.

This example shows that although the RCPA value generally decreases with time, an approximately double or triple difference exists between sample types.

Also, in this case, the sample having a larger degree of reduction in the RCPA value can be evaluated to have a higher degree of what is called "crispness", while the smaller degree of reduction in the RCPA value, the longer the taste is sustained.

Also, the quality determining function unit 255 has the function of determining the quality of a sample from the measurement result data.

The data export function unit 256 has the function of outputting "prt", "abs", "dat", and "dyn" in "csv" format.

In this case, "prt", "abs", "dat", and "dyn" are each a name of the extension of the file used with this taste recognition apparatus and have the function as an extension described below.

First, "prt" is an extension of the file for storing the result of rearranging the contents of the data of "dat" providing the measurement/analysis result in a way easily visible by human being and calculating the average value and the variations (standard deviation), and so on.

Also, "abs" is an extension of the file for storing the output of each sensor from the reference electrode for all the solutions. Only one data, i.e. the measurement setting time is stored in a file with this extension, and in normal analysis, the file stored with this extension is not used.

Also, "dyn" is an extension of the file for storing the output of each sensor from the reference electrode for all the solutions. The data stored in a file with this extension cover all the values measured every second, and in normal analysis, the file stored with this extension is not used.

Also, "dat" is an extension of the file for storing the output difference from the "stabilization liquid" immediately before sample measurement.

The data stored in a file with this extension is the measurement setting time alone. In normal analysis, the file stored with this extension is used and the result of processing such as analysis is also held with this extension.

Also, the "csv" format designates a format in which the data stored are separated with "comma", and by storing the data in this format, the reading and the editing work with Excel (registered trademark) is made possible on the part of the client (administrator terminal) 227.

Also, the estimated value calculation function unit 257 has the function (including the addition of the estimated value calculation formula) of automatically calibrating the estimated value calculation formula.

Also, the multiple regression analysis function unit 258 has the function of applying the multiple regression analysis.

Also, the graph overall function unit 259 has the function of outputting the file for the graphs in general.

The file output by the graph overall function unit 259 includes a two-dimensional scatter diagram having an enlargement function, a radar chart having the function of automatic adjustment of the number of display sensors, a three-dimensional scatter diagram, a bubble graph, a contour line graph, a sequential line graph, a transient response display graph and a measurement result graph.

Also, the history function unit 2510 includes the function units of history storage, history reproduction, macro registration, macro reproduction, partial history registration and partial history reproduction.

Also, the basic characteristic analysis function unit 2511 includes each basic characteristic analysis function unit including a no-correction function for the basic characteristic analysis.

Also, the initialization function unit 2512 has an initialization function with a management tool.

Next, the transition of the client (terminal 227) screen, i.e. the management server screen will be explained with reference to a case in which the server 220 is accessed from the client (terminal 227) and by retrieving the application for measurement setting installed in the measurement setting application 224, the administrator sets the measurement conditions, etc.

Figure 7:
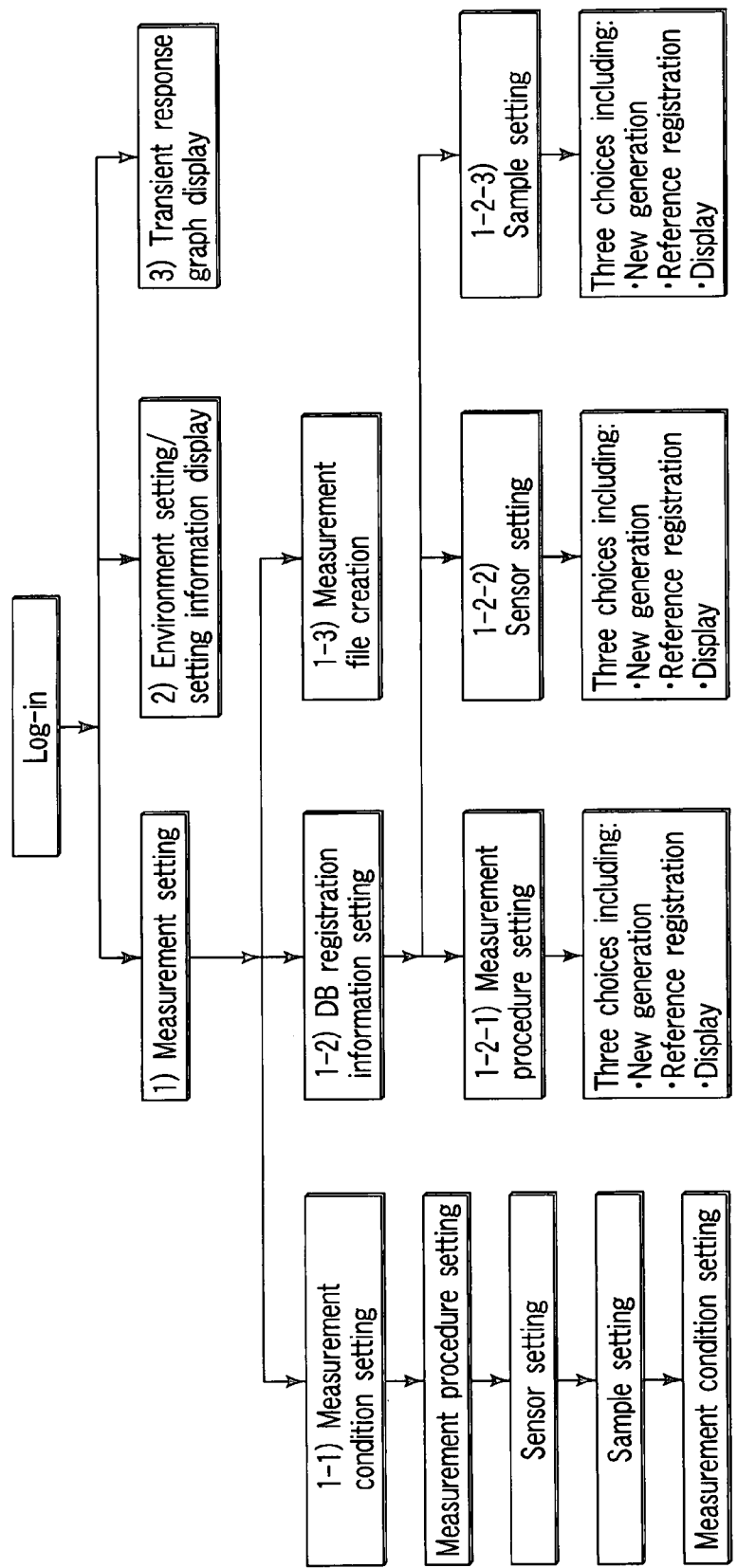
FIG. 7 is a flowchart shown for explaining the transition of a client (management terminal 227) screen, i.e. a management server screen used by an administrator to set the measurement conditions, etc. (or to analyze the measurement result) by accessing the application for measurement setting installed in a measurement setting application 224 of the server 220 (or the application for measurement result analysis installed in the analysis application 225).

FIG. 7 is a flowchart for explaining the transition of the client (terminal 227) screen (hereinafter referred to as the management server screen) in the case where the administrator sets the measurement conditions (or analyzes the measurement result), etc. by retrieving the application for measurement setting (or the application 225 for analyzing the measurement result) installed in the measurement setting application 224.

Specifically, once the client (terminal 227) is first logged in, the management server screen displays three choice screens including 1) measurement setting, 2) environment setting/setting information display, and 3) transient response graph display.

Now, assume that the administrator selects 1) measurement setting. The management server screen displays 1-1) measurement condition setting, 1-2) data base (DB) registration information setting, and 1-3) measurement file creation.

Also assume that the administrator selects 1-1) measurement condition setting. The management server screen displays the screens of measurement procedure setting, sensor setting, sample setting and measurement condition setting sequentially, and the administrator makes an appropriate setting each time.

Also assume that the administrator selects 1-2) data base (DB) registration information setting. The management server screen displays 1-2-1) measurement procedure setting, 1-2-2) sensor setting and 1-2-3) sample setting.

Assume that the administrator selects 1-2-1) measurement procedure setting. The management server screen displays three choices of new preparation, reference registration and display.

This is also true with the case in which the administrator selects 1-2-2) sensor setting or 1-2-3) sample setting.

Figure 8:
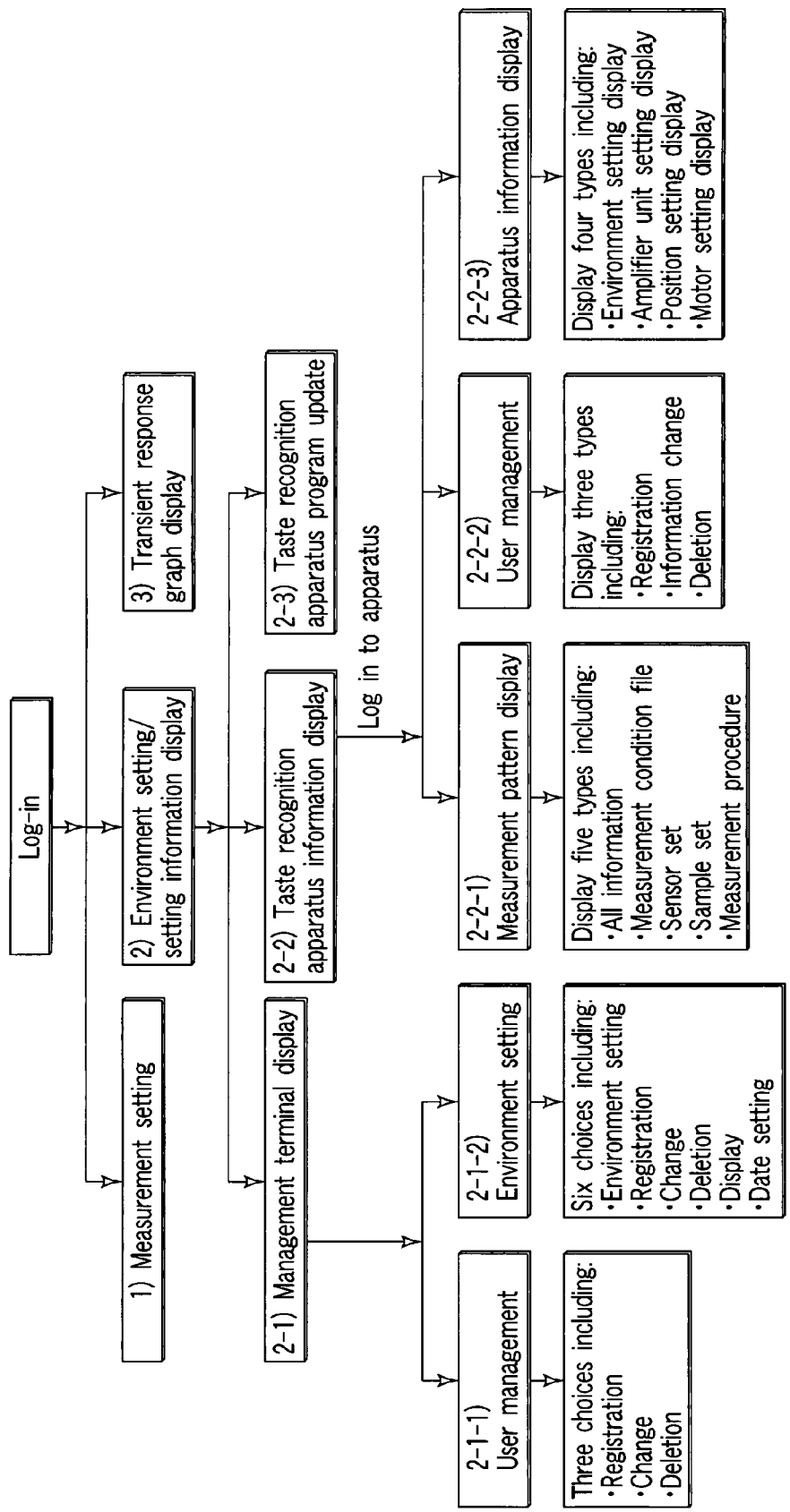
FIG. 8 is a flowchart shown for explaining the transition of the client (administrator terminal 227) screen, i.e. the management server screen used by the administrator to set the measurement conditions, etc. (or to analyze the measurement result) by accessing the application for measurement setting installed in the measurement setting application 224 of the server 220 (or the application for measurement result analysis installed in the analysis application 225).

FIG. 8 is a flowchart shown for explaining the transition of the client (terminal 227) screen, i.e. the management server screen in the case where the administrator sets the measurement conditions (or analyzes the measurement result), etc. by accessing the application for measurement setting (or the application 225 for measurement result analysis) installed in the measurement setting application 224.

Specifically, once the client (terminal 227) is first logged in, the management server screen displays three choice screens including 1) measurement setting, 2) environment setting/setting information display, and 3) transient response graph display.

Now, assume that the administrator selects 2) environment setting/setting information display. The management server screen displays three choice screens including 2-1) management terminal display, 2-2) taste recognition apparatus information display and 2-3) taste recognition apparatus program update.

Assume that the administrator selects 2-1) management terminal display. The management server screen displays a screen of two choices including 2-1-1) user management and 2-1-2) environment setting.

Assume that the administrator selects 2-1-1) user management. The management server screen displays three choices of registration, change and deletion of users.

Assume that the administrator selects 2-1-2) environment setting, on the other hand. The management server screen displays six choices including environment setting, registration, change, deletion, display and date change.

Assume that the administrator selects 2-2) taste recognition apparatus information display, on the other hand. On condition that the choice is logged in the taste recognition apparatus, the management server screen displays three choices including 2-2-1) measurement pattern display, 2-2-2) user management and 2-2-3) apparatus information display.

Assume that the administrator selects 2-2-1) measurement pattern display. The management server screen displays five choices of all information, measurement condition file, sensor set, sample set, and measurement procedure Assume that the administrator selects 2-2-2) user management. The management server screen displays three choices of registration, information change and deletion.

Assume that the administrator selects 2-2-3) apparatus information display. The management server screen displays four choices including environment setting display, amplifier (amplifier unit) setting display, position setting display and motor setting display.

Figure 9:
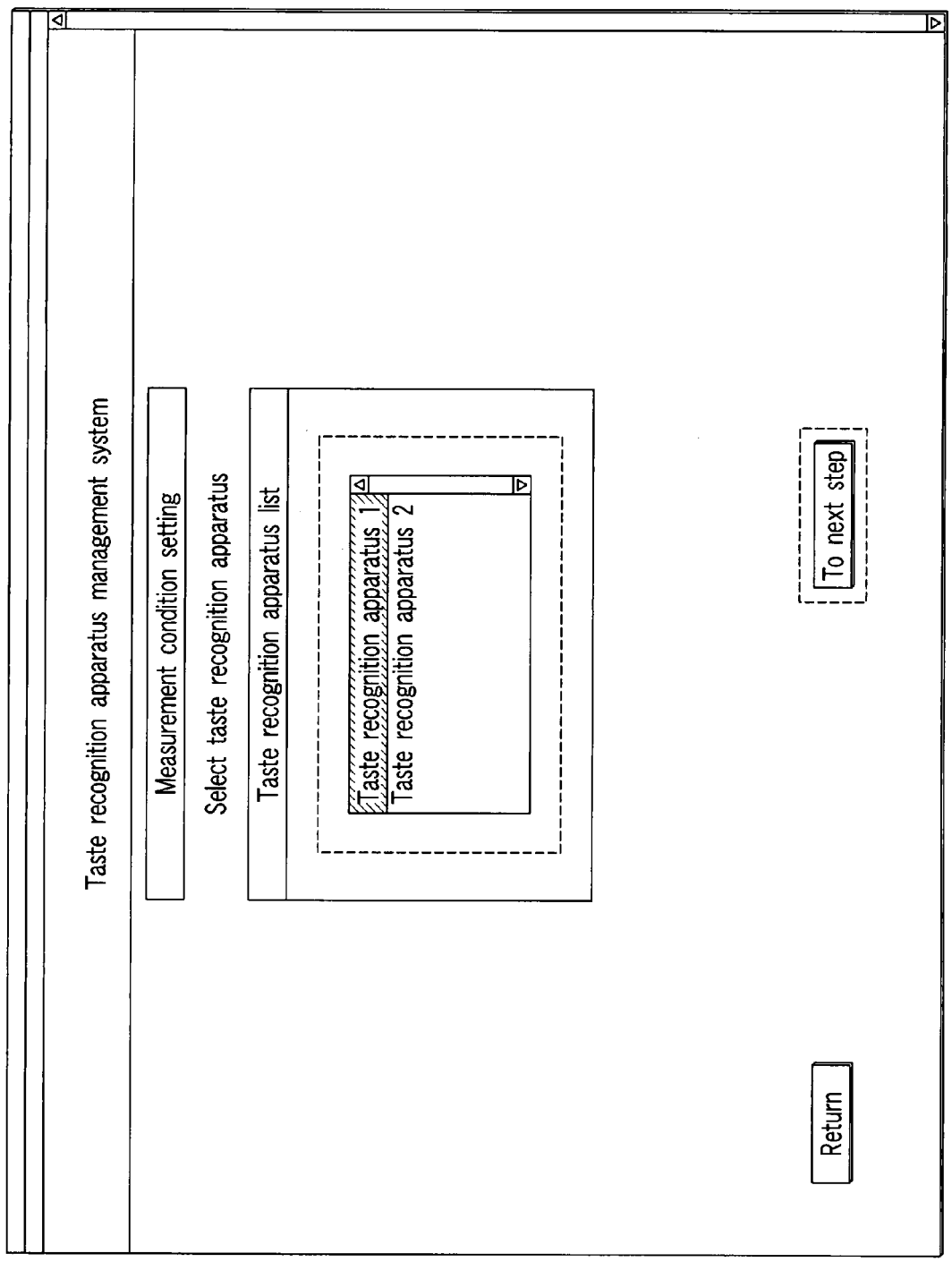
FIG. 9 is a diagram shown for explaining a measurement condition setting screen shown in 1-1 of FIG. 8.

FIG. 9 is a diagram shown for explaining the 1-1) measurement condition setting screen in FIG. 8.

Specifically, in the screen shown in FIG. 9, the administrator selects the taste recognition apparatus 2, for example, from the taste recognition apparatus list as a taste recognition apparatus for setting the measurement conditions and designates a "to next step" button.

FIG. 10 is a diagram shown for explaining the screen for selecting a place for storing the measurement conditions in FIG. 8.

Specifically, in the screen shown in FIG. 10, the administrator selects the place for storing the measurement conditions from the storage places 1 to 5, and designates the "to next step" button.

Figure 11:
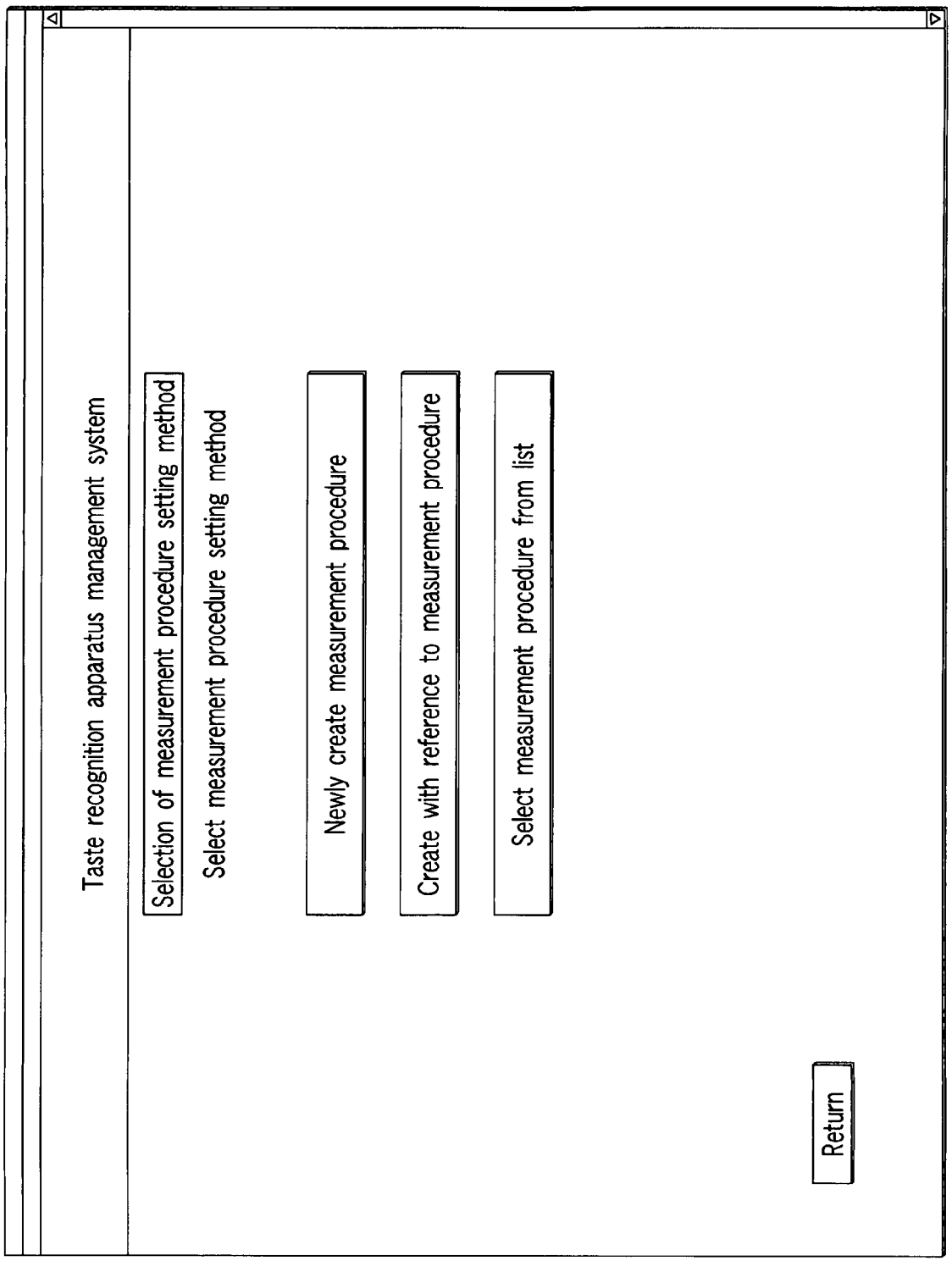
FIG. 11 is a diagram shown for explaining a screen for selecting the method of setting the measurement procedure in FIG. 8.

FIG. 11 is a diagram shown for explaining the screen permitting the administrator to select a method of setting the measurement procedure in FIG. 8.

Specifically, in the screen shown in FIG. 11, the administrator selects, as a method for setting the measurement procedure, the setting/measurement procedure from the three choices in the list with reference to new setting of the measurement procedure and the measurement procedure, and designates the "to next step" button.

Figure 12:
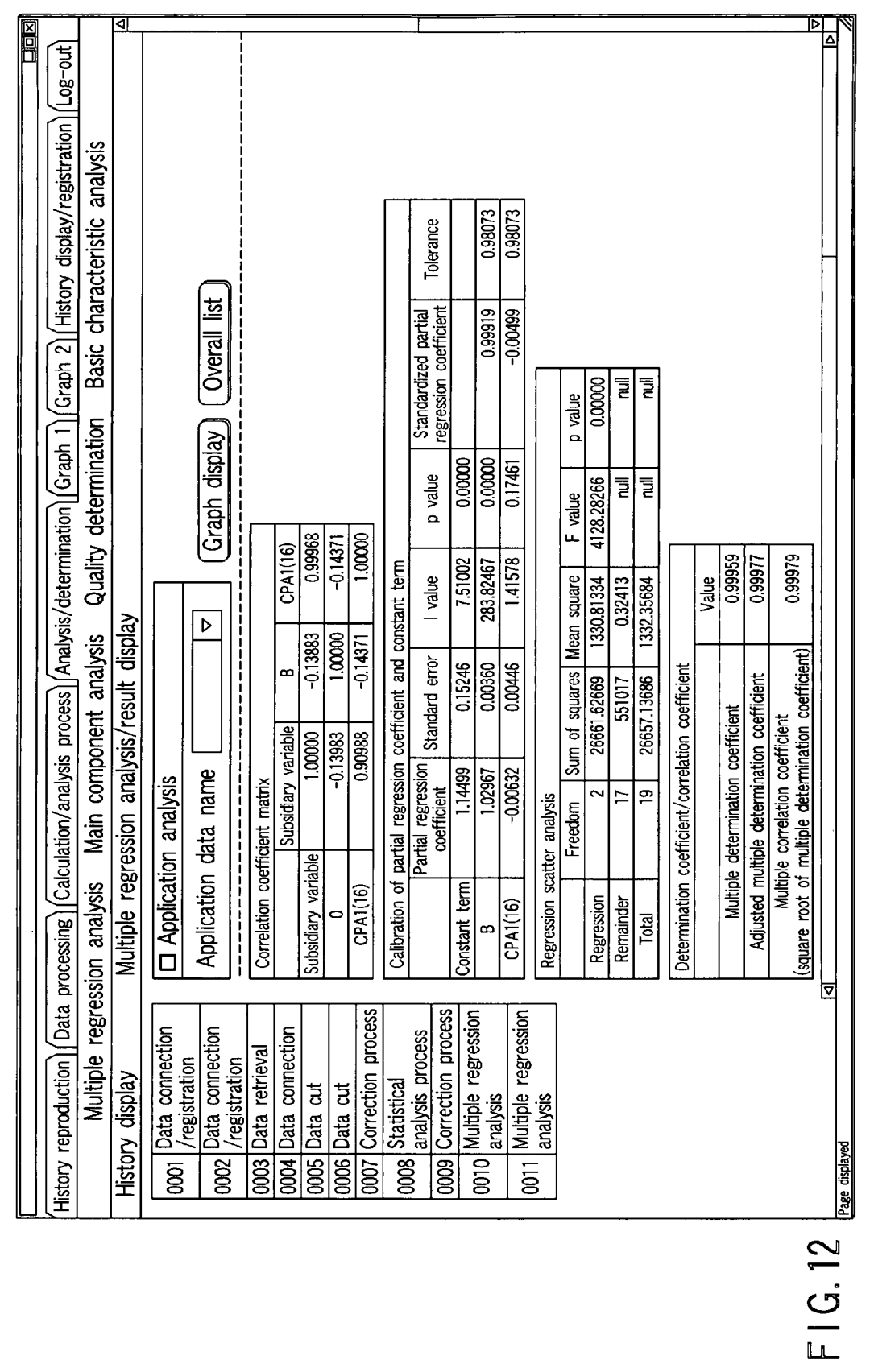

FIG. 12 is a diagram shown for explaining the screen of the result of multiple regression analysis in the multiple regression analysis function unit 258 attached to the analysis application 225 for measurement result analysis as an example of the case in which the administrator selects 3) transient response graph display in FIG. 8.

Specifically, FIG. 12 shows, as the result of multiple regression analysis, the calibration of correlation coefficient matrix, partial regression coefficient and constant term, regression scatter analysis, determination coefficient and correlation coefficient each in digital table format.

Figure 13:
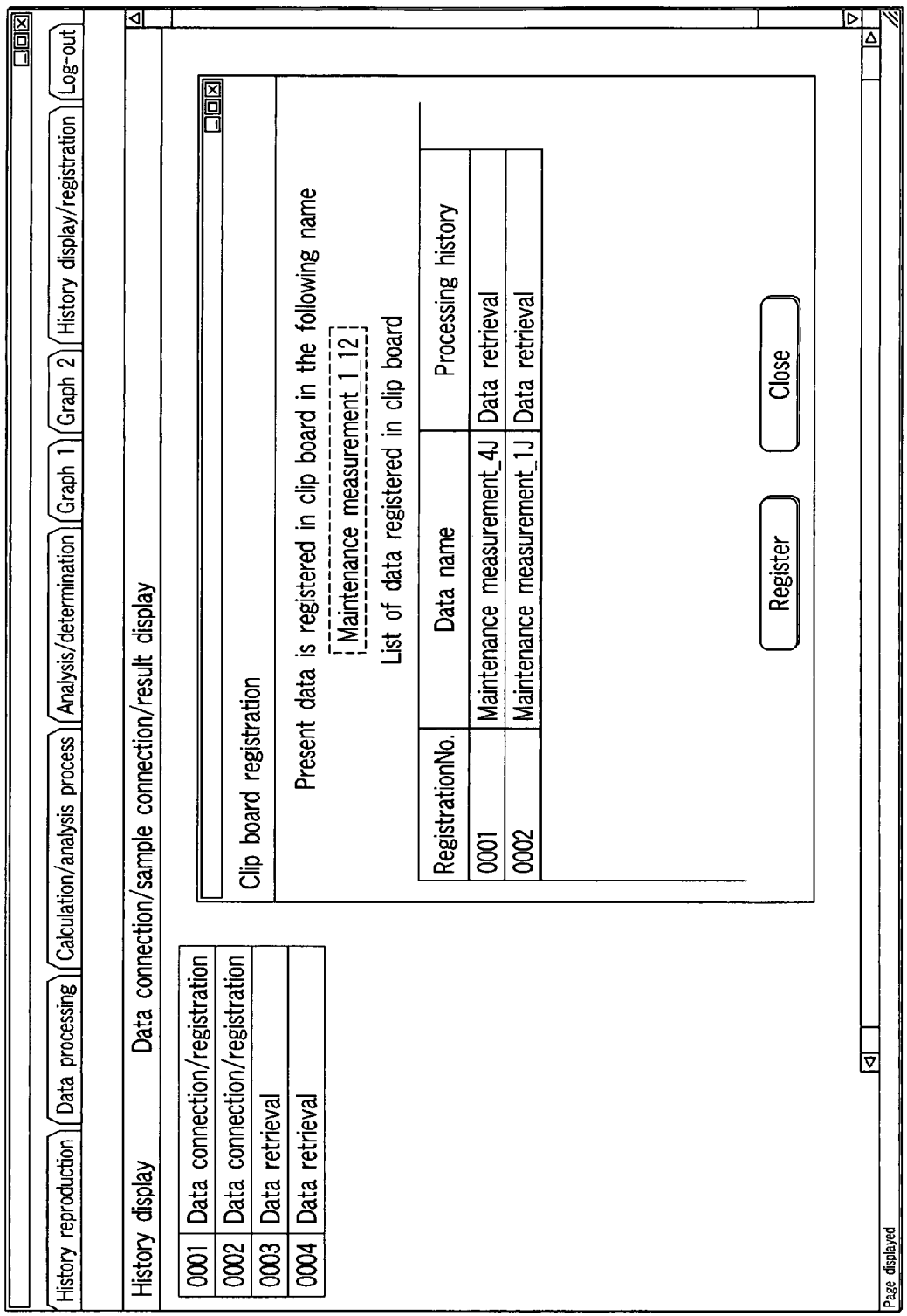
FIG. 13 is a diagram shown for explaining a clip board registration screen in the case of using a clip board function unit 253 attached to the analysis application 225 for analyzing the measurement result in FIG. 8.

FIG. 13 is a diagram shown for explaining the clip board registration screen for using the clip board function unit 253 attached to the analysis application 225 for measurement result analysis in FIG. 8.

Specifically, FIG. 13 shows the maintenance measurement 1 12 as an example of registration of the present data in the clip board with the next name.

Figure 14:
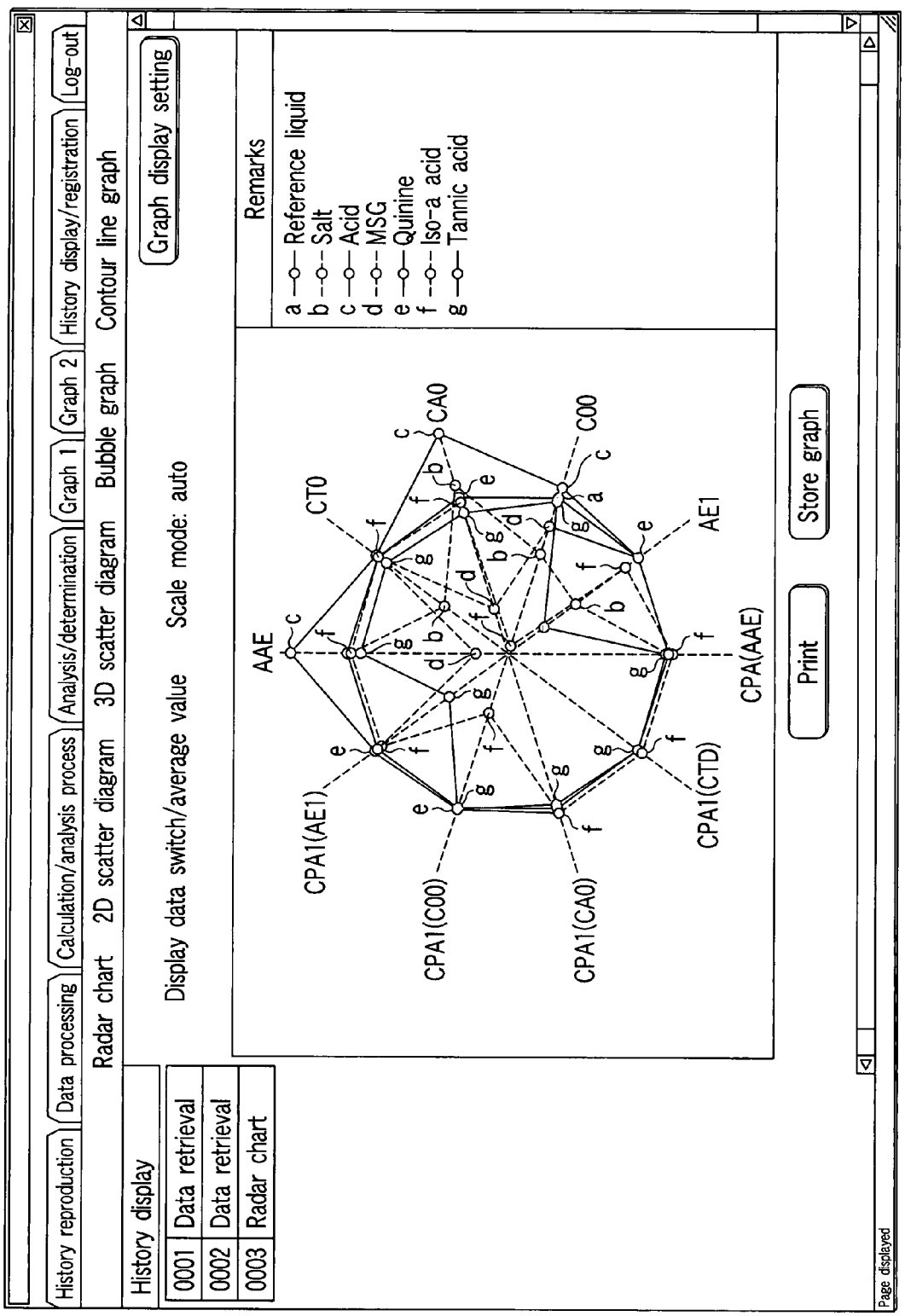
FIG. 14 is a diagram shown for explaining a radar chart screen having a function of automatic adjustment of the number of display sensors as an example of the file output from a graph overall function unit 259 attached to the analysis application 225 for analyzing the measurement result as an example of a case in which the transient response graph display is selected in (3) of FIG. 8.

FIG. 14 is a diagram shown for explaining the radar chart screen having the function of automatically adjusting the number of display sensors as an example of the file output by the graph overall function unit 259 attached to the analysis application 225 for analyzing the measurement result as an example of the case where 3) transient response graph display is selected in FIG. 8.

Specifically, FIG. 14 shows, as an example of radar chart as an index of the taste recognition information, a: reference liquid, b: salt, c: acid, d: MSG, e: quinine, f: iso-α acid and g: tannic acid based on the data AAE, CT0, CA0, CO0, AE1, CPA1 (AAE), CPA1 (CT0), CPA1 (CA0), CPA1 (C00) and CPA1 (AE1) obtained by taste measurement conducted on a given sample.

Next, the operation of the device proper 210 performed by the operator based on the transition of the screen of the touch panel 211 of the device proper 210 will be explained.

Figure 15:
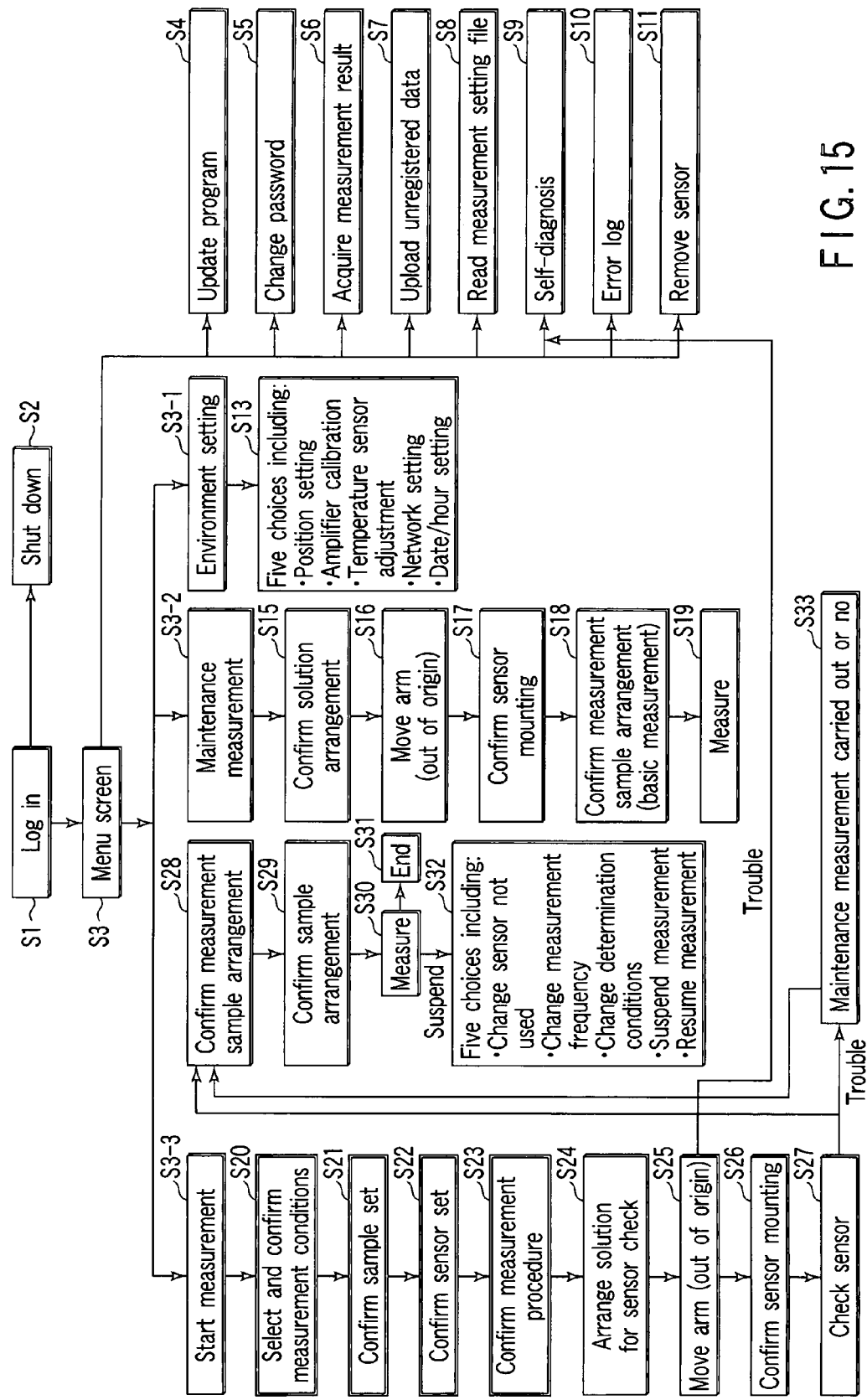
FIG. 15 is a flowchart shown for explaining the transition of the screen of the touch panel 211 of the device proper 210 and the operation of the device proper 210 operated by the operator based on the screen transition.

FIG. 15 is a flowchart shown for explaining the transition of the screen of the touch panel 211 of the device proper 210 and the operation of the device proper 210 performed by the operator based on the screen transition.

Specifically, once the touch panel 211 (device proper 210) is first logged in in step S1, the menu screen is displayed on the touch panel 211 in step S3 in other than the case of shutdown in step S2.

Incidentally, prior to display of the menu screen in step S3, the routine work such as program update (step S4), password change (step S5), measurement result acquisition (step S6), unregistered data upload (step S7), measurement setting file read (step S8), self-diagnosis (step S9), error log (step S10) and the sensor removal (step S11) is executed as required.

The menu screen displayed on the touch panel 211 in step S3 is a screen for selecting three choices including environment setting of step S3-1, maintenance measurement of step S3-2 and measurement start (normal measurement) of step S3-3.

In the case where the environment setting of step S3-1 is selected by the operator, a screen of five choices including position setting, amplifier calibration, temperature sensor adjustment, network setting and date/hour setting is displayed, and the operator selects and executes the required items.

Also, in the case where the operator selects the maintenance measurement of step S3-2, commands for solution arrangement confirmation of step S15, arm (drive unit) movement (out of origin) of step S16, sensor mounting confirmation of step S17, measurement sample arrangement confirmation (basic measurement) of step S18 and measurement of step S19 are sequentially displayed on the screen, and therefore, the operator executes each command.

Also, in the case where the operator selects the measurement start (normal measurement) of step S3-3, commands for measurement condition selection and confirmation of step S20, sample set confirmation of step S21, sensor set confirmation of step S22, measurement procedure confirmation of step S23, sensor check solution arrangement of step S24, arm (drive unit) movement (out of origin) of step S25, sensor mounting confirmation of step S26, sensor check of step S27, measurement sample arrangement confirmation of step S28, sample arrangement confirmation of step S29 and measurement of step S30 are sequentially displayed on the screen, and therefore, the operator executes each command.

Upon completion of measurement, the end of step S31 is displayed on the screen.

Incidentally, in the case where the measurement of step S30 is suspended, a screen of five choices including change of the sensor not used, change of the frequency of use, change in the determination conditions, suspension of measurement and resumption of measurement is displayed, and the operator selects and executes the required items.

Also, in the case where a trouble occurs in the arm (drive unit) movement (out of origin) of step S25, the self-diagnosis of step S9 is carried out.

Also, in the case where a trouble occurs in the sensor check of step S27, a screen of two choices of whether the maintenance measurement is to be carried out or not in step S33 is displayed.

In the case where the operator selects "to carry out the maintenance measurement", as in the case where the maintenance measurement of step S3-2 is selected above, the commands for the solution arrangement confirmation of step S15, the arm (drive unit) movement (out of origin) of step S16, the sensor mounting confirmation of step S17, the measurement sample arrangement confirmation (basic measurement) of step S18 and the measurement of step S19 are sequentially displayed on the screen, and the operator executes them in accordance with each command.

In the case where the operator determines that the trouble is no problem and selects "no maintenance measurement is to be carried out" in the sensor check of step S27, the commands for the measurement sample arrangement confirmation of step S28, the sample arrangement confirmation of step S29 and the measurement of step S30 are sequentially displayed on the screen, and the operator executes them in accordance with each command.

Incidentally, the flow of the maintenance measurement of step S3-2 includes none of the steps including the measurement condition selection and confirmation of step S20, the sample set confirmation of step S21, the sensor set confirmation of step S22 and the measurement procedure confirmation of step S23 shown in solid frames in the flow of the measurement start (normal measurement) of step S3-3.

Figures 16, 17:
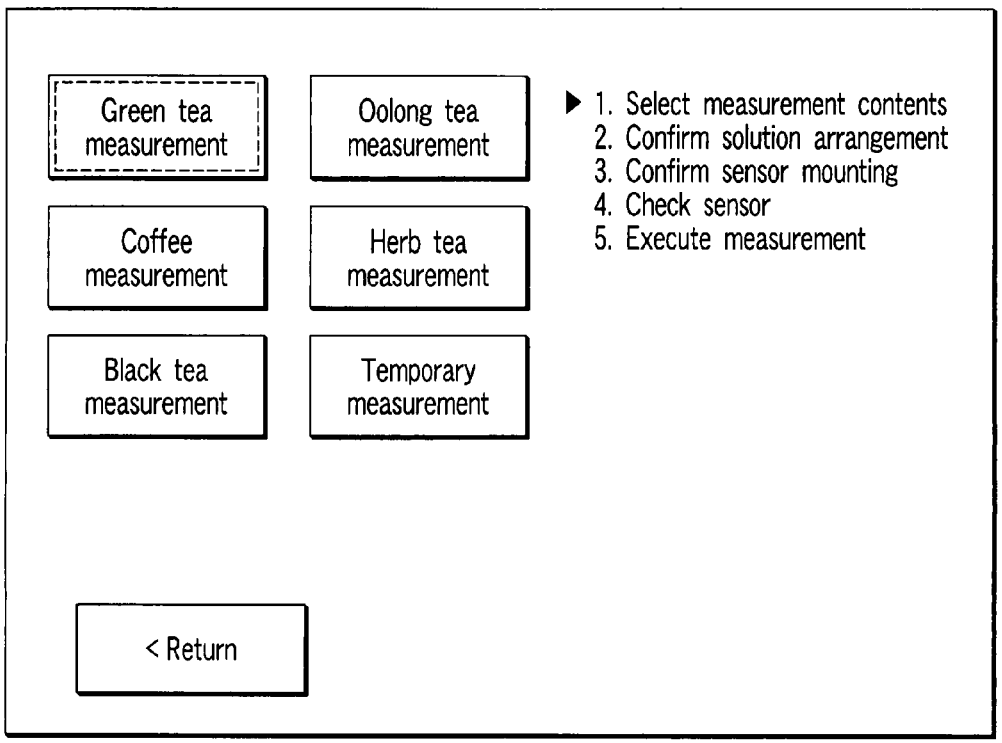
FIG. 16 is a diagram shown for explaining a "measurement content confirmation" screen as a screen for executing "measurement condition selection/confirmation" in step S20 in the case where the operator selects measurement start (normal measurement) of step S3-3 shown in FIG. 15.
FIG. 17 is a diagram shown for explaining the "measurement content confirmation" screen as a screen for executing the "measurement condition selection/confirmation" in step S20 of FIG. 15 in the case where the operator selects the measurement start (normal measurement) of step S3-3 shown in FIG. 15.
Figure 18:
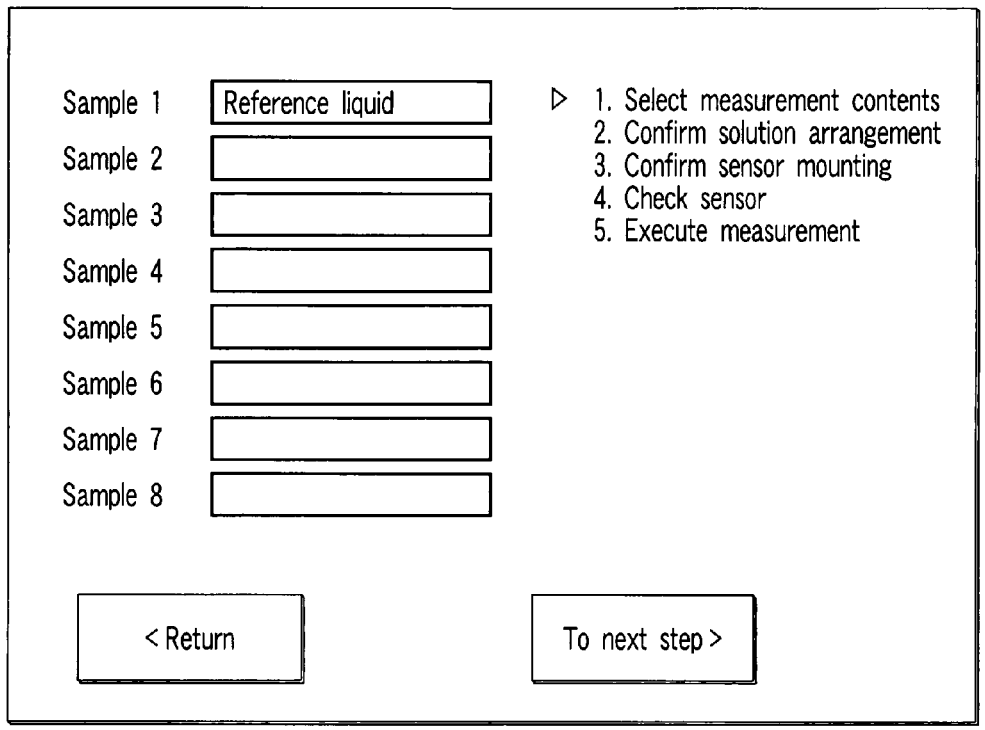
FIG. 18 is a diagram shown for explaining the "measurement content confirmation" screen as a screen for executing the "measurement condition selection/confirmation" in step S20 in the case where the operator selects the measurement start (normal measurement) of step S3-3 shown in FIG. 15.

FIGS. 16 to 18 are diagrams shown for explaining a "measurement contents confirmation" screen as a screen to execute the "measurement condition selection and confirmation" of step S20 in the case where the operator selects the measurement start (normal measurement) of step S3-3.

First, as the measurement names displayed on the "measurement contents confirmation" screen shown in FIG. 16, the button of the measurement name to be executed by the operator (assume "green tea measurement" here) is clicked out of, for example, "green tea measurement", "oolong tea measurement" "coffee measurement", "herb tea measurement", "black tea measurement" and "temporary measurement".

Next, as shown in FIG. 17, the screen displays the number of times the measurement is conducted (assume "3" times here), the sample set name (assume "test sample 1" here), the sensor set name (assume "green tea sensor set" here); the procedure book name (assume "test procedure 1" here) and the name of the measurement to be carried out (assume "green tea measurement" here), and the operator having confirmed them designates the "to next step" button.

Next, as shown in FIG. 18, the screen displays the names of samples 1 to 8 to be used for measurement (only "reference liquid" is shown here as sample 1), and the operator confirms them and designates the "to next step" button.

By way of explanation, the screen display and operations of the sample set confirmation of step S21, the sensor set confirmation of step S22, the measurement procedure confirmation of step S23, the sensor check solution arrangement of step S24, the arm (drive unit) movement (out of origin) of step S25, the sensor mounting confirmation of step S26, the sensor check of step S27 and the measurement sample arrangement confirmation of step S28 will not be explained.

Figure 19:
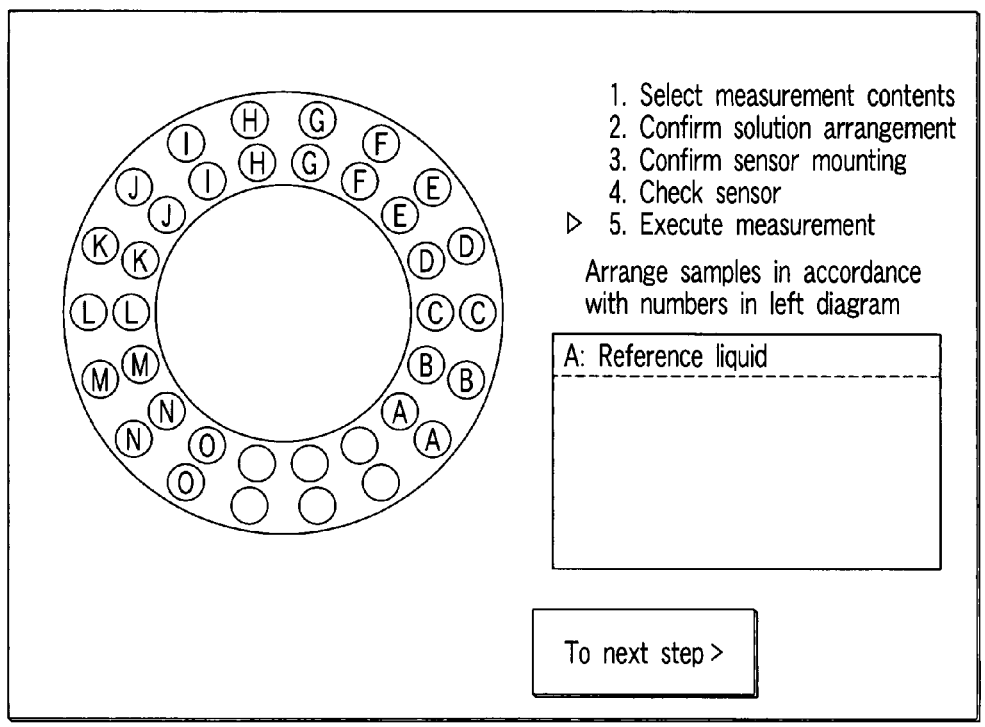
FIG. 19 is a diagram shown for explaining a screen for executing "sample arrangement confirmation" of step S29 in the case where the operator selects the measurement start (normal measurement) of step S3-3 in FIG. 15.
Figure 20:
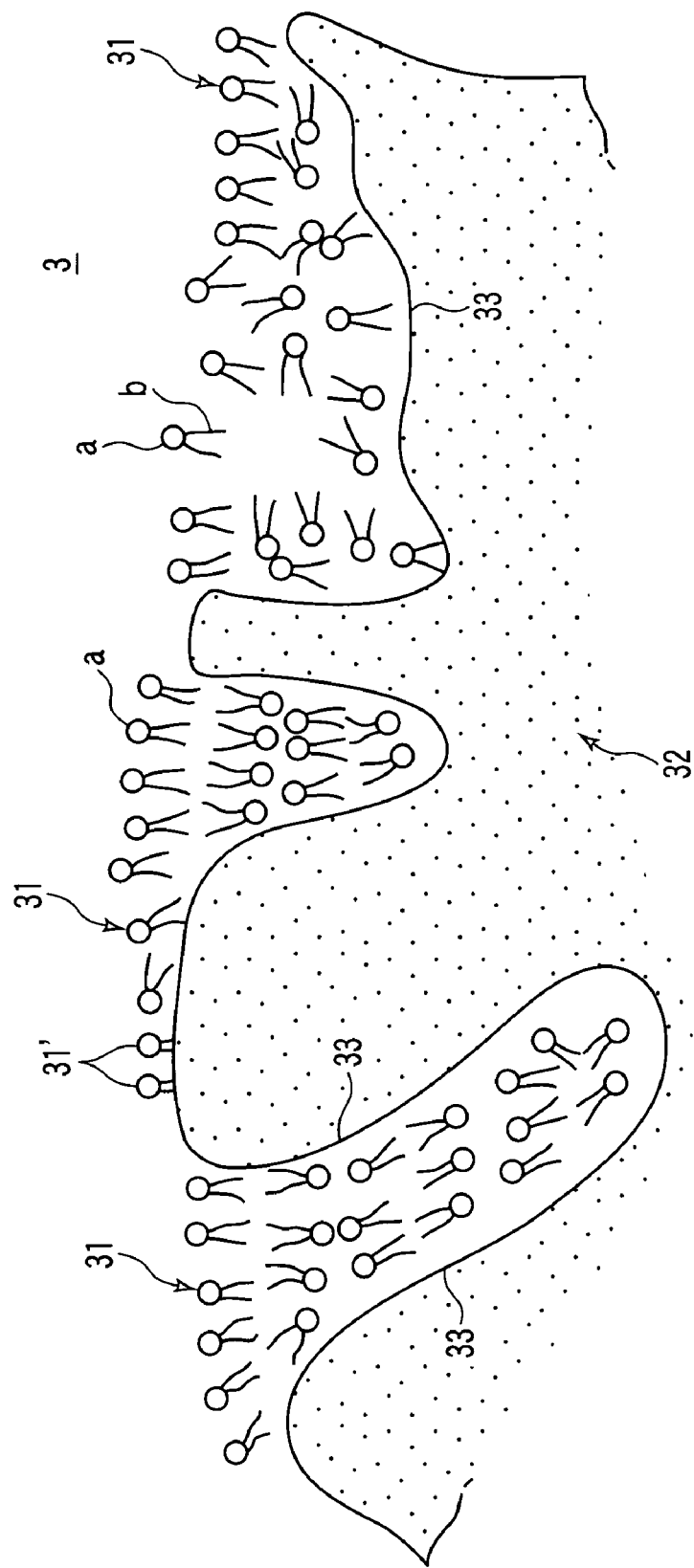
FIG. 20 is a diagram showing an expression method used as a method of designing a chemical substance to explain the schematic diagram of the lipid substance molecular film disclosed in Patent Document 1 as a conventional taste recognition apparatus.
Figure 21A:
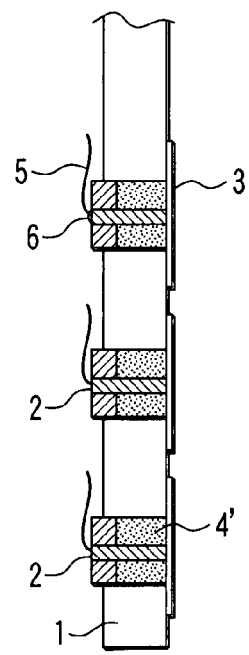
FIG. 21A is a sectional view shown for explaining three sensory units of an array electrode of a multi-channel taste sensor configured of the lipid substance molecular film disclosed in Patent Document 1 as a conventional taste recognition apparatus.
Figure 21B:
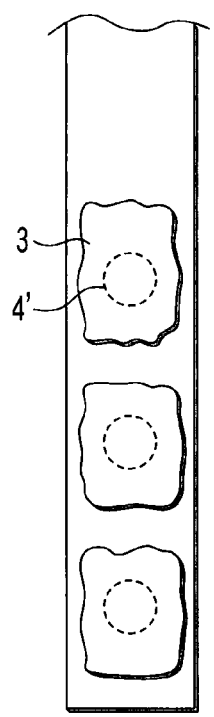
FIG. 21B is a plan view shown for explaining the three sensory units of the array electrode of the multi-channel taste sensor configured of the lipid substance molecular film disclosed in Patent Document 1 as a conventional taste recognition apparatus.
Figure 22:
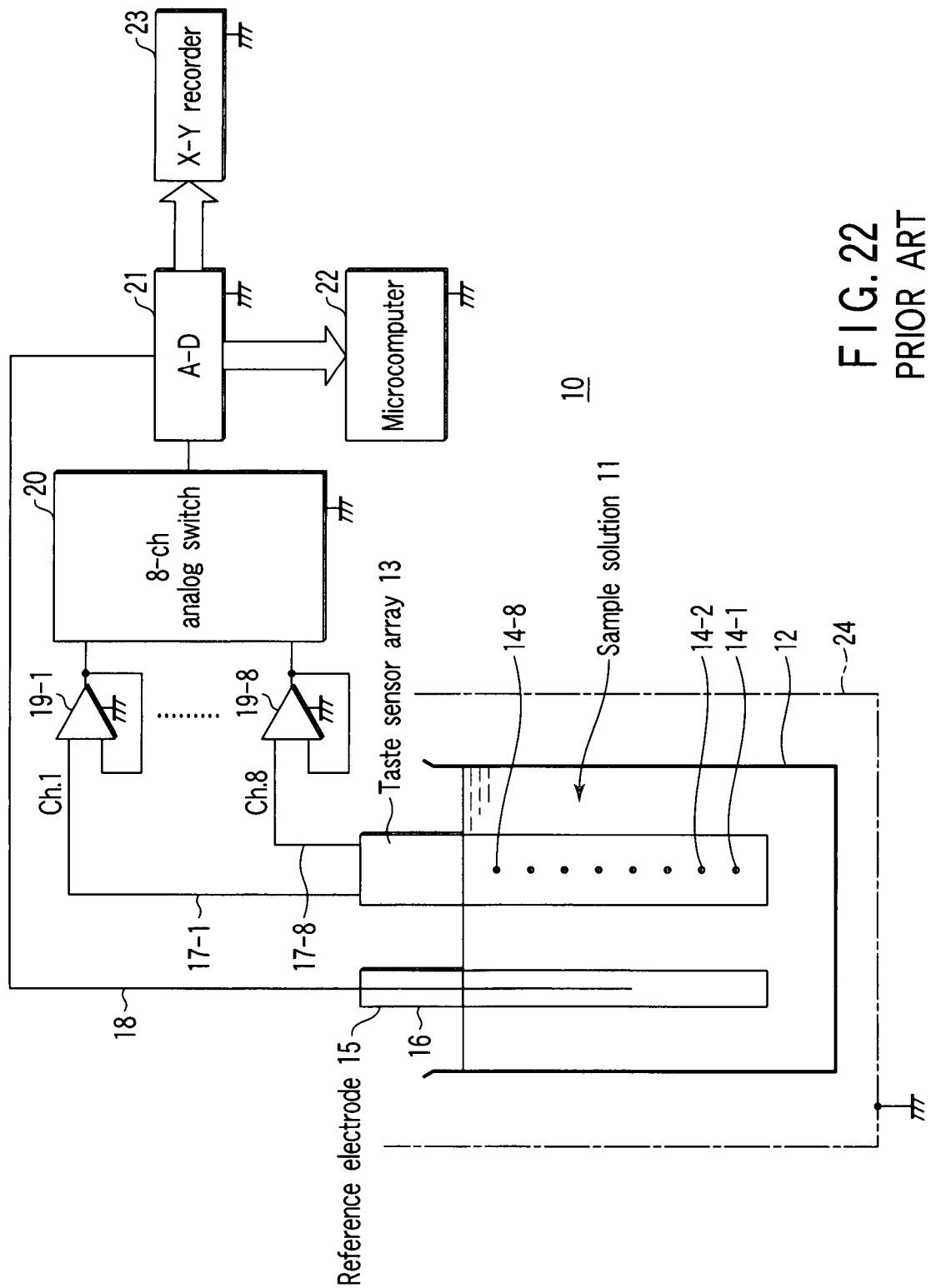
FIG. 22 is a block diagram shown for explaining a taste measurement system using the multi-channel taste sensor disclosed in Patent Document 1 as a conventional taste recognition apparatus.

FIG. 19 is a diagram shown for explaining the screen to execute the "sample arrangement confirmation" of step S29 in the case where the operator selects the measurement start (normal measurement) of step S3-3.

Specifically, FIG. 19 shows a screen for designating the sample arrangement in a plurality of solution inserting portions 321, and the operator arranges the sample including the sample taste solution and the standard sample solution and the cleaning solution for the plurality of inserting portions 321 of the solution insertion unit (213) in such an arrangement as shown on this screen.

In FIG. 19, the arrangement of predetermined samples including the sample taste solution and the standard sample solution and the cleaning solution at the encircled positions of A, B, . . . , O is designated (in this case, assume that the encircled position A is designated for arrangement of the standard sample solution).

Once the predetermined samples including the sample taste solution and the standard sample solution and the cleaning solution are arranged as designated on the screen of the touch panel 211, the operator designates the "to next step" button.

By way of explanation, the measurement of step S30, the completion of step S31, the measurement suspension of step S32, the screen display "to conduct maintenance measurement or not" of step S33 and the operation thereof will not be described.

According to an embodiment of the invention described above, therefore, in keeping with the demand to solve the problem in the background art described above, there are provided a taste recognition apparatus and a taste recognition system using the apparatus realized by a taste sensor device with lipid molecular films and a taste sensing system using the device employing a technique in which both the taste measurement of a sample taste substance and the analysis and evaluation of the taste measurement result are facilitated with a simpler operation as a whole while at the same time securing a high maintainability.

Incidentally, the taste sensor device 210 with lipid molecular films as a taste recognition apparatus and a taste recognition system using the apparatus according to an embodiment of the invention may be configured in such a manner that the touch panel 211 is arranged not independently of the sensor proper 212 but may be mounted in the console of the sensor proper 212.

INDUSTRIAL APPLICABILITY

The taste can be measured by analyzing the main component, for example, from an output signal of a sensor and classifying by comparing it with a sample having made the learning in advance. By displaying this main component two-dimensionally and preparing a taste map on the display, the sample distribution can be visually grasped from the map, thereby facilitating the classification of the sample and the comparison with sensory data.

As an alternative to the analysis of the main component, the multiple regression analysis may be carried out.

Also, as disclosed in Jpn. Pat. Appln. KOKAI Publication No. 5-99896, the sensitivity of each sensor to each original taste is determined and the sensor response is formed as a model (specifically, simultaneous equations are formed from each sensor output and sensitivity with the strength of each original taste as an unknown number), and the numerical value obtained by the calculations quantifying the strength of each original taste is corrected to a value indicating the strength of each original taste conforming with the human taste. In this way, the taste can be digitized.

According to the present invention, therefore, a panelist can be strongly supported in the quality control of beverages and beverage products or at the time of developing a new product, and the analysis/identification accuracy and the development efficiency can be remarkably improved.

The invention claimed is:

1. A taste recognition apparatus comprising:
a sensor device including:
a sensor unit provided with a sensor probe for taste measurement with a molecular film which outputs an electrical signal presenting taste information of at least one type, wherein the taste measurement includes a normal measurement mode, a maintenance measurement mode carried out before the normal measurement mode, and a sensor check mode carried out before the maintenance measurement mode;
a solution insertion unit provided with a plurality of inserting portions arranged at predetermined intervals along a circumference for selective insertion of a sample taste solution, a reference taste solution, and a cleaning solution; and
an arm drive unit which moves the sensor unit to a predetermined one of the inserting portions of the solution insertion unit, wherein based on the electrical signal presenting the taste information output from the sensor probe, measurement for taste recognition of at least the sample taste solution is made possible;
a CPU board which controls the sensor device; and
a touch panel having a display screen, wherein the CPU board controls the display screen to display operation items required for the measurement for taste recognition on the sensor device, wherein the operation items are indicated by buttons with respective functions and sequentially displayed on the display screen, and wherein when a user clicks a predetermined button, the corresponding one of the operation items can be input while at the same time permitting the user to perform all the operations on the sensor device based on the display on the display screen;
wherein the CPU board is configured to: (i) carry out the sensor check mode to confirm whether or not the taste measurement is properly conducted by the sensor unit, (ii) control the sensor unit to carry out the normal measurement mode upon confirmation that the taste measurement is properly carried out by the sensor unit in execution of the sensor check mode, (iii) control the sensor unit to carry out the maintenance measurement mode upon confirmation of "NG", indicating that the taste measurement cannot be properly carried out by the sensor unit in the execution of the sensor check mode, and (iv) carry out the maintenance measurement mode in which a basic measurement and a basic measurement analysis for analyzing a result of the basic measurement are carried out on the reference taste solution, and based on a result of the basic measurement analysis, the sensor probe of the sensor unit is cleaned to thereby carry out the sensor check mode again.

2. The taste recognition apparatus according to claim 1, wherein:
the arm drive unit is provided with an arm-like sensor board having a lower part which is projected so as to be extended in a substantially horizontal direction, and which is movable along a direction of arrangement of the solution insertion unit, and in a substantially vertical direction,
the sensor unit is supported on the lower part of the arm drive unit and is so movable with the arm-like sensor board as to insert the sensor probe in an inserting portion and remove the sensor probe from said inserting portion, and
a potential difference generated by dipping the sensor probe of the sensor unit into the sample taste solution or the reference taste solution in a predetermined one of the plurality of inserting portions is converted by an electrical circuit portion of the arm-like sensor board into digital data as the electrical signal presenting the taste information and sent out in a serial form to the CPU board which controls the sensor device.

3. The taste recognition apparatus according to claim 2, further comprising a processor mounted on the CPU board, wherein the processor is of autonomous control type.

4. The taste recognition apparatus according to claim 1, wherein the display on the touch panel is a graphic user interface (GUI) of wizard type.

5. The taste recognition apparatus according to claim 2, wherein the sensor unit includes a temperature sensor and a position sensor, and the CPU board includes a processor mounted on the CPU board, wherein the processor controls an amplifier arranged in the electrical circuit portion of the arm-like sensor board to carry out at least one of gain and offset calibration of the amplifier, controls the sensor unit to carry out calibration of the temperature sensor with an output calibration temperature sensor signal, and controls the arm drive unit to carry out a position adjustment by the position sensor arranged in the sensor unit.

6. The taste recognition apparatus according to claim 2, further comprising a processor mounted on the CPU board, wherein the processor is configured to execute a program having a self-diagnosis function of performing at least one of a hardware check including periodic confirmation of a trouble of the electrical circuit portion of the arm-like sensor board and a connection/disconnection check of a wire of each part and monitoring of a trouble of a measurement result of the sensor unit.

7. The taste recognition apparatus according to claim 6, wherein the processor mounted on the CPU board, due to the self-diagnosis function thereof, is adapted to issue an alarm upon detection of a trouble of each part and prompt a user to conduct a required maintenance work.

8. The taste recognition apparatus according to claim 4, wherein the touch panel displays a screen for designating arrangement of samples including the sample taste solution and the reference taste solution and arrangement of the cleaning solution in the plurality of inserting portions of the solution insertion unit.

9. The taste recognition apparatus according to claim 1, wherein the touch panel is provided independently of the sensor device.

10. A taste recognition system comprising:
a sensor device including:
a sensor unit provided with a sensor probe for taste measurement with a molecular film which outputs an electrical signal presenting taste information of at least one type, wherein the taste measurement includes a normal measurement mode, a maintenance measurement mode carried out before the normal measurement mode, and a sensor check mode carried out before the maintenance measurement mode;

a solution insertion unit provided with a plurality of inserting portions arranged at predetermined intervals along a circumference for selective insertion of a sample taste solution, a reference taste solution, and a cleaning solution; and an arm drive unit which moves the sensor unit to a predetermined one of the inserting portions of the solution insertion unit, wherein based on the electrical signal presenting the taste information output from the sensor probe, measurement for taste recognition of at least the sample taste solution is made possible;

a CPU board which controls the sensor device;

a touch panel having a display screen, wherein the CPU board controls the display screen to display operation items required for the measurement for taste recognition on the sensor device, wherein the operation items are indicated by buttons with respective functions and sequentially displayed on the display screen, wherein when a user clicks a predetermined button, the corresponding one of the operation items can be input while at the same time permitting the user to perform all the operations on the sensor device based on the display on the display screen, and wherein the CPU board is configured to: (i) carry out the sensor check mode to confirm whether or not the taste measurement is properly conducted by the sensor unit, (ii) control the sensor unit to carry out the normal measurement mode upon confirmation that the taste measurement is properly carried out by the sensor unit in execution of the sensor check mode, (iii) control the sensor unit to carry out the maintenance measurement mode upon confirmation of "NG" indicating that the taste measurement cannot be properly carried out by the sensor unit in the execution of the sensor check mode, and (iv) carry out the maintenance measurement mode such that a basic measurement and a basic measurement analysis for analyzing a result of the basic measurement are carried out on the reference taste solution, and based on a result of the basic measurement analysis, the sensor probe of the sensor unit is cleaned to thereby carry out the sensor check mode again; and a server which is provided with a data base and which is installed with a measurement setting application required for the measurement for taste recognition by the sensor device, and an analysis application required to analyze a result of the measurement for taste recognition by the sensor device, wherein the server is adapted to store therein various data required for the measurement for taste recognition and various data required to analyze the result of the measurement for taste recognition.

11. The taste recognition system according to claim 10, further comprising at least one management terminal which carries out various settings for the taste recognition by the sensor device by accessing the server through a network and running the measurement setting application and the analysis application installed in the server, while at the same time making it possible to carry out the analysis of the result of the measurement for taste recognition by the sensor device.

12. The taste recognition system according to claim 10, wherein the server is connected to another sensor device having a same configuration as that of said sensor device, and wherein said plural sensor devices are centrally managed by said single server.

13. The taste recognition system according to claim 10, wherein:

the arm drive unit is provided with an arm-like sensor board having a lower part which is projected so as to be extended in a substantially horizontal direction, and which is movable along a direction of arrangement of the solution insertion unit, and in a substantially vertical direction, the sensor unit is supported on the lower part of the arm drive unit and is so movable with the arm-like sensor board as to insert the sensor probe in an inserting portion and remove the sensor probe from said inserting portion, and a potential difference generated by dipping the sensor probe of the sensor unit into the sample taste solution or the reference taste solution in a predetermined one of the plurality of inserting portions is converted by an electrical circuit portion of the arm-like sensor board into digital data as the electrical signal presenting the taste information and sent out in a serial form to the CPU board which controls the sensor device.

14. The taste recognition system according to claim 13, further comprising a processor mounted on the CPU board, wherein the processor is of autonomous control type.

15. The taste recognition system according to claim 10, wherein the display on the touch panel is a graphic user interface (GUI) of wizard format.

16. The taste recognition system according to claim 13, wherein the sensor unit includes a temperature sensor and a position sensor, and the CPU board includes a processor mounted on the CPU board, wherein the processor controls an amplifier arranged in the electrical circuit portion of the arm-lime sensor board to carry out at least one of gain and offset calibration of the amplifier, controls the sensor unit to carry out calibration of the temperature sensor with an output calibration temperature sensor signal, and controls the arm drive unit to carry out a position adjustment by the position sensor arranged in the sensor unit.

17. The taste recognition system according to claim 13, further comprising a processor mounted on the CPU board, wherein the processor is configured to execute a program having a self-diagnosis function of performing at least one of a hardware check including periodic confirmation of a trouble of the electrical circuit portion of the arm-like sensor board and a connection/disconnection check of a wire of each part and monitoring of a trouble of a measurement result of the sensor unit.

18. The taste recognition system according to claim 17, wherein the processor mounted on the CPU board, due to the self-diagnosis function thereof, is adapted to issue an alarm upon detection of a trouble of each part and prompt a user to conduct a required maintenance work.

19. The taste recognition system according to claim 15, wherein the touch panel displays a screen for designating arrangement of samples including the sample taste solution and the reference taste solution and arrangement of the cleaning solution in the plurality of inserting portions of the solution insertion unit.

20. The taste recognition system according to claim 10, wherein the measurement setting application and the analysis application installed in the server are of Servlet type, a setting method is of wizard type, and data storage is of data base type.

21. The taste recognition system according to claim 10, wherein:

a measurement procedure by the measurement setting application includes sensor post-processing, cleaning determination and sensor processing, in that order, the sensor post-processing is executed such that in order to remove a substance attached to a lipid substance film in the sensor probe of the sensor unit due to previous measurement, the sensor probe is moved into and out of a plurality of different cleaning solutions an appropriate number of times to thereby execute a cleaning process, the cleaning determination is carried out such that in order to determine a quality of the cleaning process by the sensor post-processing, a result of the cleaning process is measured for each of the plurality of different cleaning solutions used in the sensor post-processing, and the taste measurement is executed in the sensor processing.

22. The taste recognition system according to claim 11, wherein data being measured for taste recognition by the sensor unit is displayed as transient response data on the touch panel, and wherein the display of the transient response data can be confirmed also on the management terminal through the server.

23. The taste recognition system according to claim 12, wherein in the case where the plurality of sensor devices with molecular films are connected to said single the server as a plurality of taste recognition apparatuses, display of all the transient response data being measured by the plurality of sensor devices with molecular films as the plurality of taste recognition apparatuses can be confirmed on of the management terminal through the server.

24. The taste recognition system according to claim 10, wherein the analysis application includes a data retrieval function unit, a data select function unit, a clip board function unit, an attenuation ratio calculation function unit, a quality determining function unit, a data export function unit, an estimated value calculation function unit, a multiple regression analysis function unit, a graph overall function unit, a history function unit, a basic characteristic analysis unit and an initialization function unit.

* * * * *